United States Patent
Yager et al.

(10) Patent No.: US 7,030,989 B2
(45) Date of Patent: Apr. 18, 2006

(54) WAVELENGTH TUNABLE SURFACE PLASMON RESONANCE SENSOR

(75) Inventors: Paul Yager, Seattle, WA (US); Elain S. Fu, Seattle, WA (US)

(73) Assignee: University of Washington, Seattle, WA (US)

( * ) Notice: Subject to any disclaimer, the term of this patent is extended or adjusted under 35 U.S.C. 154(b) by 113 days.

(21) Appl. No.: 10/696,738

(22) Filed: Oct. 28, 2003

(65) Prior Publication Data

US 2004/0130723 A1 Jul. 8, 2004

Related U.S. Application Data

(60) Provisional application No. 60/421,917, filed on Oct. 28, 2002.

(51) Int. Cl.
*G01N 21/55* (2006.01)

(52) U.S. Cl. ............................................. 356/445
(58) Field of Classification Search ............. 356/445, 356/446, 447, 448
See application file for complete search history.

(56) References Cited

U.S. PATENT DOCUMENTS

| | | | | |
|---|---|---|---|---|
| 4,804,271 A | * | 2/1989 | Cammann | 356/416 |
| 5,229,833 A | * | 7/1993 | Stewart | 356/364 |
| 5,313,264 A | * | 5/1994 | Ivarsson et al. | 356/73 |
| 5,322,798 A | * | 6/1994 | Sadowski | 356/317 |
| 5,339,155 A | * | 8/1994 | Partridge et al. | 356/437 |
| 5,351,127 A | * | 9/1994 | King et al. | 356/445 |
| 5,485,277 A | * | 1/1996 | Foster | 356/445 |
| 5,491,556 A | * | 2/1996 | Stewart et al. | 356/445 |
| 6,330,062 B1 | * | 12/2001 | Corn et al. | 356/445 |
| 6,493,097 B1 | * | 12/2002 | Ivarsson | 356/630 |
| 6,573,107 B1 | * | 6/2003 | Bowen et al. | 356/317 |
| 2003/0048452 A1 | * | 3/2003 | Johansen | 356/445 |
| 2004/0036881 A1 | * | 2/2004 | Sharma et al. | 356/445 |

FOREIGN PATENT DOCUMENTS

| | | | |
|---|---|---|---|
| WO | WO 01/69209 A1 | * | 9/2001 |
| WO | WO 02/059602 A2 | | 8/2002 |

OTHER PUBLICATIONS

Kovacs, G. (1982), "Optical excitation of surface plasmon-polaritons in layered media," *Electromagnetic Surface Modes*, Boardman, A.D. (ed.), John Wiley & Sons Ltd., pp 144–200.

Naimushin, A.N. et al. (2002), "Detection of *Staphylococcus aureus* enterotoxin B at femtomolar levels with a miniature integrated two–channel surface plasmon resonance (SPR) sensor," Biosensor Bioelectron. 17:573–584.

(Continued)

*Primary Examiner*—Zandra V. Smith
*Assistant Examiner*—Juan D. Valentin, II
(74) *Attorney, Agent, or Firm*—Townsend and Townsend and Crew LLP

(57) ABSTRACT

This invention provides methods, devices and device components for sensing, imaging and characterizing changes in the composition of a probe region. More particularly, the present invention provides methods and devices for detecting changes in the refractive index of a probe region positioned adjacent to a sensing surface, preferably a sensing surface comprising a thin conducting film supporting surface plasmon formation. In addition, the present invention provides methods and device for generating surface plasmons in a probe region and characterizing the composition of the probe region by generating one or more surface plasmon resonances curves and/or surface plasmon resonance images of the probe region.

71 Claims, 13 Drawing Sheets

OTHER PUBLICATIONS

Schuck, P. (1997), "Use of Surface Plasmon Resonance to Probe the Equilibrium and Dynamic Aspects of Interactions Between Biological Macromolecules," Annu. Rev. Biophys. Biomol. Struct. 26:541–566.

Welford, K. (1991), "Surface plasmon–polaritons and their uses," Opt. Quant. Electron. 23:1–27.

Begley, D.L. and Seery, B.D., "Narrowband optical interference filters" (1991) Free–Space laser communication technologies III, SPIE Proceedings, vol. 1417:525–536.

Berger, C. E. H., R. P. H. Kooyman, et al. (1994). "Resolution in surface plasmon microscopy." *Review of Scientific Instruments* 65(9): 2829–2836.

Berning, Peter H., (1963) "Theory and calculations of optical thin films," *Physics of Thin Films*, G. Hass, New York, Academic Press 1:69–120.

Brockman, J. M.et al. (2000), "Surface plasmon resonance imaging measurements of ultrathin organic films." *Annual Reviews of Physical Chemistry* 51:41–63.

de Bruijn, H. E.et al. (1992), "Choice of metal and wavelength for surface–plasmon resonance sensors: some considerations." *Applied Optics* 31(4): 440–442.

de Bruijn, H. E.et al. (1993), "Surface plasmon resonance microscopy: improvement of the resolution by rotation of the object." *Applied Optics* 32(13): 2426–2430.

Fu, E. et al. (Jun. 2003), "Wavelength–tunable surface plasmon resonance microscope," *Rev. Sci. Instruments* 74(6):3182–3184.

Hickel, W. and W. Knoll (1991), "Time and spatially resolved surface plasmon optical investigation of the photodesorption of Langmuir–Blodgett multilayer assemblies." *Thin Solid Films* 199:367–373.

Hickel, W. and W. Knoll (1990), "Surface plasmon microscopy of lipid layers." *Thin Solid Films* 187:349–356.

Nelson, B.P. et al., (1999), "Near–infrared surface plasmon resonance measurements of ultrathin films. 1. Angle shift and SPR imaging experiments," Anal. Chem. 71(18):3928–3934.

Rothenhäusler, B. and W. Knoll (1988), "Surface–plasmon microscopy." *Letters to Nature* 332(14): 615–617.

* cited by examiner

Fig. 13A
Fig. 13B
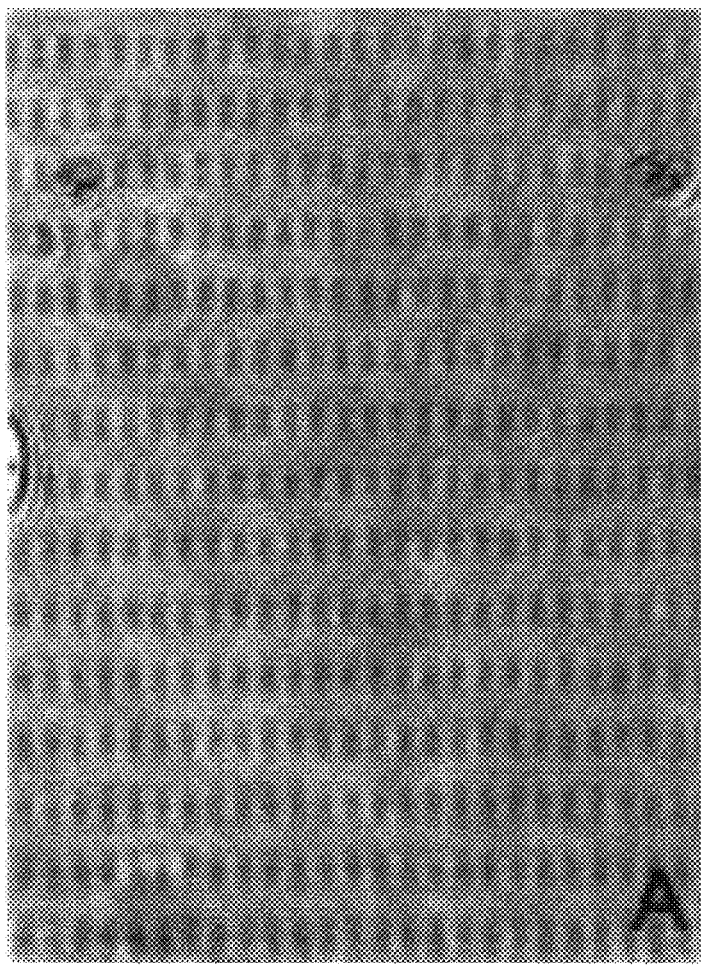
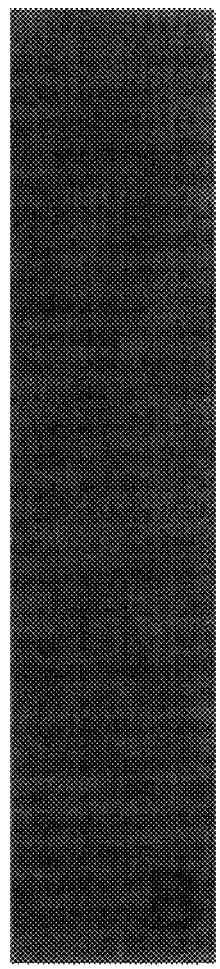

WAVELENGTH TUNABLE SURFACE PLASMON RESONANCE SENSOR

CROSS-REFERENCE TO RELATED APPLICATIONS

This application claims priority under 35 U.S.C. 119(e) to provisional patent application 60/421,917, filed Oct. 28, 2002, which is hereby incorporated by reference in its entirety to the extent not inconsistent with the disclosure herein.

STATEMENT REGARDING FEDERALLY SPONSORED RESEARCH OR DEVELOPMENT

The work was funded through a grant by the United States government under NIDCR grant 1UO1 DE14971-01.

BACKGROUND OF THE INVENTION

Surface plasmon resonance (SPR) microscopy is a technique that uses excitation of surface plasmons (SPs) to detect chemical and physical changes in a probed region adjacent to a sensing surface. A variety of sensors based on SPR techniques have been developed which provide a sensitive means of characterizing the thickness and index of refraction of ultrathin films occurring at the surface of a thin metal film. In recent years, SP sensors have been used extensively to characterize chemical and physical properties of a variety of biological materials and to probe binding events in real time. For example, SP sensors have been used successfully to characterize the morphology of a range of surfaces, probe the kinetics and dynamics of interactions between proteins, proteins and DNA and proteins and small molecules, monitor antibody-antigen binding and characterize DNA hybridization processes.

Surface plasmons, also know as surface plasmon waves or plasmon polaritons, are charge density waves, which propagate parallel to an interface between a conducting or semiconducting thin film and a dielectric sample layer. SPs are generated by coupling radiant energy from incident photons into the oscillating modes of free electrons present in a conducting material, such as a metal, or semiconductor material. SPs are highly localized at the surface of the conducting (or semiconducting) layer and the intensity of the electric field of a SP decays exponentially in directions perpendicular to the plane in which it propagates. The spatial distribution of a SP may be quantitatively described by a characteristic decay length corresponding to the distance over which the intensity of the SP decays to $e^{-1}$ times its value at the conductor (or semiconductor)—dielectric sample layer interface. Decay length (L) is provided by the expression:

$$L = \frac{1}{2\mathrm{Re}\left(\sqrt{k_{sp}^2 + k_s^2}\right)}; \qquad (\mathrm{I})$$

wherein Re refers to the real part of the quantity in parentheses, $k_{sp}$ is the surface plasmon wavevector and $k_s$ is the wavevector in the dielectric sample layer adjacent to the conductor (or semiconductor). For a dielectric sample layer comprising water and a conducting thin film comprising gold the decay length is equal to about 83.1 nm for light having a wavelength of about 632.8 nm. The highly localized nature of SPs make them ideally suited for detecting very small changes in refractive index occurring in sensing regions proximate to a sensing surface ($\leq$ about 300 nm).

In conventional SPR methods, a SP is excited by evanescent electromagnetic waves generated upon total internal reflection of an incident light beam. In the Kretschmann-Raether geometry, evanescent electromagnetic waves penetrate a thin metal film ($\approx$50 nm) positioned between higher and lower refractive index dielectric layers and excite a SP, which propagates parallel to the outer surface of the metal film adjacent to the lower refractive index layer. The prism is needed to achieve the wavevector matching condition between the incident excitation light and the surface plasmons. For a given dielectric sample, photons of a certain wavelength and incident at a certain angle will generate evanescent waves that penetrate the metal layer and excite surface plasmons at the metal-dielectric sample interface. The intensity of reflected light will therefore be reduced and can be monitored as a signal of SP generation. Alternatively, in the Otto SPR configuration, the metal layer and prism are separated by an air gap and SPs are excited on the side of the metal film adjacent to the prism. A drawback of the Otto SPR configuration is that it is experimentally difficult to maintain a very thin and constant thickness air gap. Finally, in other SPR methods, surface plasmons are created by evanescent fields generated as light propagates down a fiber optic or waveguide having a thin metal interior layer Excitation of SPs via total internal reflection is a resonant phenomenon that depends on the wavevector of the incident light (i.e. both the wavelength and angle of incidence of the incident light beam. In addition, excitation of SPs is dependent on the indices of refraction and thickness of the higher refractive index layer, lower refractive index sample layer and conducting (or semiconducting) thin film used to couple radiant energy into the oscillating modes of free electrons present in the conductor. The dispersion equation for a SP is provided by the equation:

$$k_{sp} = k_0 \sqrt{\frac{\varepsilon_c \varepsilon_d}{\varepsilon_c + \varepsilon_d}}; \qquad (\mathrm{II})$$

wherein $k_0$ is the free space wavevector ($k_0 = \omega/c$); $\in_c$ and $\in_d$ are the complex permittivities of the conducting (or semiconducting) thin film and the lower refractive index dielectric sample layer, respectively and $\omega$ is the angular frequency. A resonance condition of exciting an SP is that the parallel component of the incident wavevector ($k_{par}$), must equal the surface plasmon wave vector ($k_{sp}$):

$$k_{par} = k_{sp} \qquad (\mathrm{III}).$$

The parallel component of the incident wavevector may be expressed in terms of the index of refraction of the medium in which the light is incident, n, the angle of incidence, θ, and the wavelength of the incident light beam, λ, by the equation for formation of a SP:

$$k_{par} = \frac{2\pi n \sin(\theta)}{\lambda}. \qquad (\mathrm{IV})$$

Substituting equations II and IV into equation III provides the following relationship expressing the resonance condition for the formation of a surface plasmon in terms of the angle of incidence and wavelength of the incident beam:

$$\frac{2\pi n \sin(\theta)}{\lambda} = k_0 \sqrt{\frac{\varepsilon_c \varepsilon_d}{\varepsilon_c + \varepsilon_d}}. \quad (V)$$

As is evident from equation V, for a given metal film thickness and set of refractive indices of dielectric layers, the resonance condition may be satisfied by variation of either the angle of incidence or the wavelength of the incident light beam, or both.

In the derivation of the dispersion relation for the SP, equation II, two additional conditions that must be satisfied for surface plasmon generation to occur become apparent. First, SPs are p-polarized and so can only be excited by p-polarized incident light. And second, SPs are only supported at an interface made up of media with real permittivites of opposite sign.

As illustrated by equations II–V, changes in the refractive index of the dielectric sample layer adjacent to the thin metal film changes the resonance condition for generating a SP. This change in resonance condition may be monitored directly by measuring the intensity of the reflected incident beam as a function of angle of incidence, wavelength of the incident beam or both. Satisfaction of the resonance condition results in a sharp attenuation in the intensity of the reflected beam caused by a conversion of radiant energy of the incident beam into SPs at the interface between the thin metal film and the lower refractive index layer. Due to their spatially localized nature, SPs have also been used to excite photoluminescent materials. Specifically, energy from a SP is coupled to a photoluminescent material in a manner resulting in excitation of an electronic transition providing fluorescence or photoluminescence. An additional detector can be positioned in optical communication with the sensing surface to measure the intensity of fluorescence of materials pumped by the SPR process. The combination of attenuated reflectance SPR methods and SPR induced fluorescence has been demonstrated to provide a sensitive means of characterizing chemical and physical changes occurring at a senor surface.

Sensors based on SPR utilize the dependence of the SPR resonance condition on changes in the refractive index of a lower refractive index dielectric sample layer positioned adjacent to the thin metal (or semiconductor) film. In typical sensing applications, changes in the resonance condition for formation of SPs are monitored in real time and directly related to chemical or physical changes occurring at a sensing surface adjacent to the thin metal (or semiconductor) film. Sensors based on SPR may provide selective detection of materials and compounds by manipulating the chemical or physical properties of the sensing surface. In these applications, the sensing surface may be coated with a material exhibiting selective binding characteristics such that the refractive index varies in the presence of a specific material to be sensed. For example, the sensing surface may be made sensitive to a particular antibody by coating it with an antigen to that antibody. Using these principles, SPR detection has been successfully incorporated into a number of commercially available biological sensing devices including the sensors and screening devices manufactured by BIAcore, Inc.

Generally, a SPR optical configuration comprises (1) a source of electromagnetic radiation, (2) an optically transmissive component having a first refractive index, (3) a dielectric sample layer (or probe region) having a second refractive index less than that of the first refractive index of the optically transmissive component, (4) a conducting or semiconducting thin film positioned between the optically transmissive component and the dielectric sample layer (probe region) and (5) a detector. In this configuration, an incident beam is transmitted through the transparent region at an angle of incidence such that it undergoes total internal reflection at the interface between the optical transmissive component and the conducting thin film. The reflected incident beam is collected and directed to a detector capable of measuring its intensity as function of time. If the resonance condition outlined in Equations II to V is met, radiant energy is converted into a SP at the interface between the conducting or semiconducting thin film and the dielectric sample layer resulting in a measurable decrease in the intensity of the reflected incident beam.

Sensors based on SPR may utilize a number of different optical configurations. Exemplary optical configurations are described in Rothenhausler, B. and W. Knoll (1988). "Surface-plasmon microscopy." *Letters to Nature* 332(14): 615–617., Hickel, W. and W. Knoll (1990). "Surface plasmon microscopy of lipid layers." *Thin Solid Films* 187: 349–356, Hickel, W. and W. Knoll (1991). "Time and spatially resolved surface plasmon optical investigation of the photodesorption of Langmuir-Blodgett multilayer assemblies." *Thin Solid Films* 199: 367–373, de Bruijn, H. E., R. P. H. Kooyman, et al. (1992), "Choice of metal and wavelength for surface-plasmon resonance sensors; some considerations." *Applied Optics* 31(4): 440–442, de Bruijn, H. E., R. P. H. Kooyman, et al. (1993). "Surface plasmon resonance microscopy; improvement of the resolution by rotation of the object." *Applied Optics* 32(13): 2426–2430, Berger, C. E. H., R. P. H. Kooyman, et al. (1994). "Resolution in surface plasmon microscopy." *Review of Scientific Instruments* 65(9): 2829–2837 and Brockman, J. M., B. P. Nelson, et al. (2001) "Surface plasmon resonance imaging measurements of ultrathin organic films." *Annual Reviews of Physical Chemistry* 51(1): 41–47, which are hereby incorporated by reference in their entireties to the extent not inconsistent with the present application.

The most common configuration in SPR sensing applications involves angle modulation of a substantially monochromatic, coherent incident light beam. In this technique, a surface plasmon resonance curve is generated by measuring the intensity of a reflected, substantially monochromatic, coherent incident beam, as the angle of incidence is systematically varied. Satisfaction of the SP resonance condition results in a measurable attenuation of the intensity of the incident beam corresponding to the minimum of a curve of reflected beam intensity versus incident angle. The angle corresponding to this minimum, referred to as the resonant angle ($\theta_{sp}$), is dependent on the index of refraction near the surface of the conducting layer. Adsorption or binding of materials in the sensing region adjacent to the conducting layer changes the index of refraction in the sensing region and causes a measurable shift in the value of $\theta_{sp}$. Quantification of the shift in $\theta_{sp}$, therefore, provides a sensitive means of observing and characterizing changes in the composition and concentration of materials in sensing region. For example, studies have demonstrated linear correlations exist between resonance angle shifts and protein concentrations in the sensing region.

Despite the demonstrated effectiveness of angle modulation SPR techniques, theses optical configurations have several practical limitations. First, angle modulation optical configurations require use of complicated optical component rotation assemblies for selectably adjusting the angle of incidence of the incident beam. Typically, such assemblies provide for rotation of a combination of a light source, beam shaping optics and polarizing optics and/or rotation of a combination of light collection optics and a detector. Optical configurations requiring use of such complex rotation assemblies are undesirable because they are costly, spatially restrictive and require frequent maintenance and realignment. Second, use of complex optical component rotation assembles increases an instrument's sensitivity to optical misalignment caused by vibration and variations in ambient temperature and pressure. Finally, use of coherent light sources, such as lasers, in angle modulation SPR techniques results in unwanted optical interference of reflected beam components. Such optical interference is undesirable because it results in fringe patterns, which substantially degrades the optical quality of images obtained by SPR techniques.

Another optical configuration common to SPR sensing applications involves wavelength modulation. In wavelength modulation optical configurations, the intensity of the reflected incident beam is monitored for a fixed angle of incidence as the wavelength of the incident beam is systematically varied. In these techniques, a surface plasmon resonance curve is generated by measuring the intensity of a reflected incident beam, as the wavelength of the incident beam is varied. The wavelength corresponding to the minimum of a curve of reflected beam intensity verse wavelength, referred to as the resonant wavelength ($\lambda_{sp}$), indicates satisfaction of the resonance condition and is dependent on the index of refraction of a sensing region adjacent to the surface of the conducting layer. Quantification of the shift in $\lambda_{sp}$, therefore, provides a sensitive means of observing and characterizing changes in the composition and concentration of materials in sensing region. SPR wavelength modulation techniques commonly employ a constant angle of incidence and, therefore, do not require use of bulky optical rotation assembles.

Another application of SPR to sensing is SPR imaging techniques, wherein spatial differences in the reflectivity of an incident beam are measured as a function of time. In this technique, a collimated, monochromatic light beam is used for excitation of SPs and reflected light corresponding to a probe region is monitored by a two-dimensional array detector, such as a charge coupled device or camera. Differences in composition in the probe region are monitored in real time by observing a two-dimensional distribution of measured reflected light intensities. The thickness and refractive index of materials absorbed or bound to certain regions of the probe area may satisfy the SP resonance condition and provide for efficient SP formation. Therefore, these regions will exhibit attenuated reflected light intensities. Other regions of the probe area, in contrast, may comprise absorbed or bound materials having refractive indices which do not satisfy the SP resonance condition and do not result in efficient SP formation. Therefore, these regions will exhibit high reflectivities of the incident beam. Differences in the reflectivities of regions having different chemical and physical properties result in an image characterizing the entire probe area. The maximum contrast between regions in the probe area can be obtained by varying the imaging angle or wavelength of the SPR system.

Brockman, J. M., B. P. Nelson, et al. (2001). "Surface plasmon resonance imaging measurements of ultrathin organic films." *Annual Reviews of Physical Chemistry* 51(1): 41–47 describes an optical configuration that is reported to improve quality and sensitivity of images generated by SPR imaging techniques. The authors disclose an optical arrangement comprising a collimated white light source, polarizer, prism—thin gold film sample assembly, narrow band interference filter and charge couple device (CCD) camera. The reference shows five SPR images corresponding to five different interference filters, which passes different wavelengths of excitation light. Although the authors report that SPR image quality may be optimized by selection of an interference filter having the appropriate transmission characteristics, the disclosed methods require time consuming, iterative image quality adjustment by manual removal and insertion of different interference filters. The authors principally depend on angle scanning to optimally contrast the samples in their probe region. Moreover, removal and insertion of optical interference filters requires repeated alignment of the excitation and detection optical arrangements. In addition, the teaching of the reference is limited to optical configurations providing discrete detection wavelength selection and does not provide the ability to tune the excitation or detection wavelength over a continuous range of values. Finally, the methods disclosed expose the sample to significant intensities of light having wavelengths not detected by the CCD camera, which do not contribute to SPR image formation and may damage materials in the probe region.

It will be appreciated from the foregoing that a clear need exists for methods and devices for generating SPs in thin conducting (or semiconducting films) which do not utilize angle modulation SPR, particularly angle modulation SPR optical configurations having complex rotational assemblies. Further, methods and devices for wavelength modulation SPR sensing and/or imaging having continuously tunable, incoherent light sources are needed. Finally, tunable SPR instruments are needed which eliminate undesirable optical interference problems and provide enhanced sensitivity and resolution.

SUMMARY OF THE INVENTION

This invention provides methods, devices and device components for sensing, imaging and characterizing changes in the composition of a probe region. More particularly, the present invention provides methods and devices for detecting changes in the refractive index of a probe region positioned adjacent to a sensing surface, preferably a sensing surface comprising a thin conducting film supporting SP formation. In addition, the present invention provides methods and device for generating surface plasmons in a probe region and characterizing the composition of the probe region by generating one or more surface plasmon resonances curves and/or surface plasmon resonance images of the probe region. The methods and devices of the present invention may be used to detect and characterize adsorption, absorption or binding of chemical species, such as molecules and ions, to a probe region, particularly a probe region having selected binding affinity and/or other selected chemical or physical properties. Further, the present invention provides wavelength tunable SPR sensing devices and imaging devices that are capable of sensing changes in the occurrence of SPR and/or the SP resonant wavelength required for SPR formation as a function of time, particularly with respect to a probe region undergoing physical and/or chemical changes. Wavelength tunable SPR sensing devices of the present invention may be used to detect species in a solution that are in contact with or near the sensing surface.

It is an object of the present invention to provide tunable SPR sensing and imaging devices that do not require angular modulation, particularly devices which do not require complex optical rotation assemblies for varying the angle of incidence in conventional angular modulation SPR optical configurations. It is further an object of the present invention to provide methods and devices which minimize the occurrence of optical interference, particularly methods and devices which eliminate the occurrence of fringe patterns and speckle which degrade SPR image quality and obfuscate SPR sensing measurements. It is yet another object of the present invention to provide methods and devices for detecting materials, such as atoms, molecules, ions or aggregates of atoms, molecules and ions, which do not require pre-detection labeling processes, such as fluorescent labeling or radioactive labeling processes.

In one aspect, the present invention provides a wavelength tunable surface plasmon resonance sensor for sensing, monitoring and characterizing changes in the refractive index of a probe region. Wavelength tunable surface plasmon resonance sensors of the present invention provide excitation light and/or detected light having a distribution of wavelengths that is selectably adjustable. An exemplary wavelength tunable surface plasmon resonance sensor comprises an incoherent, polychromatic light source, a polarizer, an SPR optical assembly, a detector and a selectably adjustable wavelength selector. In these embodiments, the polychromatic light source is positioned in optical communication with the polarizer and SPR optical assembly. Light generated by the light source propagates along an incident light propagation axis and is directed through a polarizer resulting in light having a selected polarization orientation, preferably substantially p-polarized light or s-polarized light. Preferred polarizers of the present invention provide a means of easily switching between incident light having a p-polarization orientation and s-polarization orientation. Light having a selected polarization orientation is directed onto the SPR optical assembly. In an exemplary embodiment, the SPR optical assembly comprises a dielectric layer, a dielectric sample layer and a conducting layer position between the dielectric layer and the dielectric sample layer. The dielectric sample layer adjacent to the conducting film comprises the probe region. Exemplary SPR sensors of the present invention further comprise one or more optical collimation elements positioned between the polychromatic light source and the SPR optical assemble for collimating the light beam directed to the SPR optical assembly.

Illumination of the SPR optical assembly at angles of incidence resulting in total internal reflection generates light propagating along a reflected light propagation axis. In exemplary configurations, light propagating along the incident light propagation axis or light propagating along the reflected light axis is passed through a selectably adjustable wavelength selector positioned in the optical path between the light source and the detector. In a preferred embodiment, the selectably adjustable wavelength selector transmits light having a distribution of transmitted wavelengths selected to generate surface plasmons on the surface of the conducting layer adjacent to the probe region. Light propagating along the reflected light axis is detected by the detector, thereby sensing the refractive index of the probe region. Optionally, light propagating along the reflected light axis may be collected by a light collection element and focused onto the detector to improve detection sensitivity and resolution.

In one embodiment, the present invention provides a means of quantifying percentage reflectivities of p-polarized incident light that is reflected from the SPR optical assembly. In an exemplary embodiment, the SPR optical assembly is alternately illuminated with p-polarized light and s-polarized light by selective adjustment of the polarizer. Illumination of the SPR optical assembly with p-polarized light having a wavelength satisfying the SP resonance condition converts radiant energy to SPs, which decreases the intensity of the reflected p-polarized light. Because s-polarized light does not result in SP formation, decreases in the intensity of reflected p-polarized light may be accurately characterized in terms of a percentage reflectivity by comparing the intensities of detected p-polarized light and s-polarized light resulting from alternative illumination of the SPR optical assembly with substantially p-polarized and s-polarized light beams.

In the present invention, the selectably adjustable wavelength selector provides wavelength tuning functionality useful for characterizing SP resonance conditions and measuring a resonant wavelength necessary for SP formation. Further, the selectably adjustable wavelength selector of the present invention eliminates the need for angular modulation for sensing changes in the refractive index of a probe region by SPR methods. In the context of this aspect of the present invention, wavelength tuning refers to selective variation of incident and/or detected light in a manner satisfying SP resonance conditions and resulting in SP excitation. As SP resonance conditions are a dependent on the refractive index of the probe region, wavelength tunable SPR sensors of the present invention provide a means of detecting and monitoring physical and chemical properties, such as composition, binding affinity and reactivity, of the probe region.

Preferred wavelength selectors provide a distribution of transmitted wavelengths that is selectably adjustable. The distribution of transmitted wavelengths of light of the present invention may be characterized in terms of a center wavelength, bandwidth and wavelength intensity profile. Exemplary wavelength selectors of the present invention are capable of selectively adjusting the center wavelength of a distribution of transmitted wavelengths over a continuum of values. In the present invention, the center wavelength, bandwidth and/or wavelength intensity profile of light transmitted by the wavelength selector may be selected to enhance the sensitive or resolution of a SPR sensing measurement. Alternatively, the center wavelength of the distribution, bandwidth and/or wavelength intensity profile of light transmitted by the wavelength selector may be selected to enhance SPR image quality (i.e. optimal refractive index contrast within different areas of the probe region).

To observe SP formation, characterize the SP resonance condition or measure the SP resonant wavelength, exemplary SPR sensors of the present invention monitor a decrease in the intensity of light reflected from the SPR optical assembly. Selectably adjustable wavelength selectors of the present invention provide a means of adjusting the wavelengths of light that are detected. This allows resonant wavelengths to be accurately measured and also allows for characterization of a SP resonance curve by measuring reflected light intensities as a function of the wavelength of light transmitted by the wavelength selector. The ability to selectively adjust the wavelengths of light that are detected provides this function of the wavelength tunable SPR sensors of the present invention. Therefore, selectably adjustable wavelength selectors of the present invention may be positioned anywhere in the optical path of collimated light from the polychromatic light source to the detector. In one embodiment, the selectably adjustable wavelength selector is positioned between the polychromatic light source and the SPR optical assembly to provide selective adjustment of the distribution of wavelengths of the excitation light directed on to the SPR optical assembly and subsequently detected.

In another embodiment, the selectably adjustable wavelength selector is positioned between the SPR optical assembly and the detector to provide selective adjustment of the distribution of wavelengths directed onto the detector and detected. The present invention also includes embodiments having additional selectably adjustable wavelength selectors, which may be positioned anywhere along the optical pathway between the polychromatic optical source and the detector. An advantage of positioning of the selectably adjustable wavelength selector between the light source and the SPR optical assembly is that only light having wavelengths that are detected by the detector are exposed to the SPR optical assembly. Reducing the intensity of light directed onto the optical assembly is beneficial for avoiding increases in temperature of the optical assembly due to illumination. Such temperature changes of the optical assembly can change the refractive index of the probe region and obscure SPR sensing measurements and images.

Selectably adjustable wavelength selectors useable in the present invention may comprise any device or device component capable of transmitting a selected distribution of transmitted wavelengths and substantially preventing the transmission of other wavelengths of light. In an exemplary embodiment of the present invention, the selectably adjustable wavelength selector is an optical interference filter, which is rotationally adjustable about a rotational axis orthogonal to the plane of incidence (also orthogonal to the incident light propagation axis or the reflected light propagation axis). In this embodiment, rotation of the optical interference filter selectably adjusts the distribution of wavelengths of light that are transmitted by the optical interference filter, particularly the center wavelength of the distribution of transmitted wavelengths. Exemplary selectably adjustable wavelength selectors of the present invention include, but are not limited to, optical interference filters, etalons, Fabry-Perot etalons, monochromators, spectrometers, prisms, gratings and linear variable interference filters. Preferred selectably adjustable wavelength selectors provide substantially the same net transmittance over a range of center wavelengths needed to measure the resonance wavelength. Preferred selectably adjustable wavelength selectors have well characterized transmission properties with respect to s- and p- polarized light. In discrete wavelength operation, wavelength tuning may be used to generate SPs that result in optimal contrast of different areas in the probe region. In wavelength scanning operation, the center wavelength of the distribution of transmitted wavelengths may be continuously varied while SPR measurements or images are collected.

Use of a selectably adjustable wavelength selector in SPR sensors of the present invention provides the ability to tune the wavelength distribution of excitation light, detected light or both. The present devices and methods provide the ability to continuously tune the wavelength distribution of excitation light, detected light or both or a substantial range of wavelength, preferably over a range of at least 60 nm and more preferably over a range of several hundred nanometers. Wavelength tunability provided by this attribute of the present invention allows changes in SPR resonance conditions to be detected and characterized as a function of time. Changes in SPR resonance condition may be directly related to the refractive index of the probe region. Therefore, wavelength tunability provided selectably adjustable wavelength selectors of the present invention allows for accurate quantification of physical and chemical characteristics of the probe region. Further, wavelength tunability also provides for a wide dynamic range of SPR sensors of the present invention. Particularly, wavelength tunable SPR sensors and imaging devices of the present invention may be used to detect and characterize a very broad range of materials having different refractive indices, thicknesses and chemical compositions. In addition, use of a selectably adjustable wavelength selector in SPR sensors of the present invention eliminates the need for angle modulation to detect changes in the SPR resonance condition or determine a resonant wavelength or distribution of resonant wavelengths. Avoiding angle modulation SPR optical configurations is beneficial because these configurations typically require complex rotational optical assemblies that are spatially restrictive, costly and sensitive to misalignment due to vibration and changes in ambient pressure and temperature. Further, avoiding optical geometries having complex rotational assemblies is beneficial because such assemblies require frequent calibration and realignment.

Use of an incoherent, polychromatic light source in the present invention has several advantages. First, use of an incoherent light source avoids problems arising from optical interference of beam components generated from the excitation and reflected beams. Optical interference affects can substantially degrade SPR sensing measurements and images due to formation of interference fringes and speckle. In addition, incoherent light sources, such as halogen lamps, are inexpensive, exhibit highly reproducible intensities and are easy to optically align.

The present methods and devices are broadly applicable to any SPR optical assembly configuration. Exemplary SPR optical assembly assemblies useable in the present invention comprises a thin metal film in contact with a prism and dielectric sample layer arranged in the Kretchmann optical geometry or the Otto optical geometry. Alternatively, sensors of the present invention may include SPR optical assemblies comprising waveguides, fiber optic devices, optical gratings or any combination of these components.

Any wavelength of light capable of generating SPs may be used in the methods and devices of the present invention. Use of light having wavelengths in the near infrared region of the electromagnetic spectrum (about 800 nm to about 1200 nm) is preferred for some SPR imaging applications because it provides increased refractive index sensitivity compared to technique using higher frequency visible light. In addition, use of the near infrared may be beneficial for certain applications wherein the probe region interrogated contains species that absorb in the visible region. In preferred embodiments, the wavelengths of light employed by SPR sensors and/or imaging devices of the present invention are selected over the range of about 845 nm to about 857 nm.

Wavelength tunable SPR sensors of the present invention may be operated in a variety of different operational modes. SPR operational modes correspond to different types of SPR measurements, different functional aspects of these devices and different methods of using these devices. Exemplary SPR sensors of the present invention are capable of operation in a plurality of operating modes.

In one operational mode, SPR sensors of the present invention are capable of measuring a distribution of resonant wavelengths resulting SP formation. In an exemplary embodiment, the selectably adjustable wavelength selector is adjusted to systematically vary the wavelength distribution of detected light in a manner generating a SP resonance curve. Preferred SP resonance curves generated by the methods and devices of the present invention comprise a two-dimensional plot of percent reflectivity versus the center wavelength of the distribution of wavelengths transmitted by the wavelength selector. Quantification of the resonant wavelength or distribution of resonant wavelengths provides information relating to the composition of a probe region because the resonance condition is strongly dependent on the refractive index of the probe region.

In another operation mode, SPR sensors of the present invention are capable of monitoring changes in the resonant wavelength or distribution of resonant wavelengths required for SP formation. Monitoring changes in the distribution of resonant wavelengths is beneficial because it provides information related to changes in the refractive index and composition occurring in the probe region, such as changes due to binding of chemical species to portions of the probe region. In one embodiment, the SPR sensor is wavelength tuned by selection of a distribution of transmitted wavelengths resulting in formation of SPs and attenuation of reflected light. The intensity and/or percentage reflectivity of reflected light is monitored as a function of time over an observation interval. Changes in the resonance condition corresponding to changes in refractive index and chemical composition of the probe region are observed and characterized by measuring a change in the intensity and/or percentage reflectivity of reflected light. Alternatively, SPR sensors of the present invention are capable of measuring changes in the resonant wavelength or distribution of resonance wavelengths by generating a plurality of resonance curves corresponding to different observation intervals and/or different experimental conditions. The measured shift in the resonant wavelength or distribution of resonant wavelengths may be directly related to corresponding changes in composition occurring in the probe region. Use of a selectably adjustable wavelength selector in these embodiments is beneficial for precisely quantifying the shift in the resonant wavelength or distribution of resonant wavelengths.

In another operation mode, a wavelength tunable SPR sensor of the present invention is capable of operation as a SPR imaging device. In this embodiment, the SPR sensor includes a two-dimensional detector, such as a charge coupled device or two-dimensional diode array. In a preferred embodiment, a p-polarized light beam having a wavelength distribution capable of exciting one or more SPs is directed at the SPR optical assembly and a first two-dimensional distribution of reflected light intensities is measured. This first two-dimensional distribution of reflected light intensities comprises an image of the probe region. In some embodiments, the distribution of reflected p-polarized light intensities must be normalized to achieve an optimal SPR image because the combination light source and wavelength selector of the present invention produces wavelength dependent transmission intensities. In methods of the present invention correcting for this effect, a s-polarized light beam is directed at the SPR optical assembly and a second two-dimensional distribution of reflected light intensities is measured. Switching between p- and s- polarization orientations is preferably achieved by adjustment of the polarizer positioned between the polychromatic light source and the SPR optical assembly. Comparison of first and second two-dimensional reflected light intensity distributions generates a SPR image, which characterizes the probe region. Preferred SPR images generated by the present methods and devices comprise a two dimension distribution of measured percent reflectivities. In an exemplary embodiment, SPR images are corrected for differences in s and p-polarization transmission properties of wavelength selectors used in the present invention, particularly transmission properties which vary as a function of rotational angle. Use of a selectably adjustable wavelength selector SPR imaging devices of the present invention is beneficial for transmitting light having distribution of transmitted wavelengths selected to provide images having enhanced optical quality and sharpness. Further, SPR imaging devices and methods of the present invention are capable of generating images exhibiting high contrast between highly reflective regions and attenuated reflection regions.

In another aspect, the present invention provides methods of detecting and characterizing chemical or physical interactions between chemical species in a probe region. Particularly, a SPR sensor of the present invention may be employed having a dielectric sample layer operationally coupled to a reactor, such as a flow cell or flow reactor, capable of effectively introducing chemical species, such as atoms, molecules or ions, into the sample dielectric layer and probe region. Exemplary reactors, are capable of generating a flow of chemical species in a solution of other delivery medium which contacts the probe region. The probe region may be constructed in a manner such that it exhibits selected chemical and/or physical properties, such as selective binding affinities, chemical reactivities and/or physical properties. For example, the second probe region may comprise a reactor having one or more target chemical species, such as biological polymers, immobilized on the reactor surface. In an exemplary embodiment, the sensing surface of the thin conducting layer is chemically modified to provide selective affinity, reactivity, bonding or other chemical and/or physical properties. Deposition of selected materials directly onto the surface of the conducting layer, such as carboxymethylated dextran, may facilitate covalent attachment of biopolymers such as proteins or oligonucleotides to sensing surfaces of the present invention. In these embodiments, introduction of one or more interacting species to the reactor may result in binding, chemical reaction or physical interaction between target and interacting species, thereby changing the refractive index in the probe region. Use of SPR sensors of the present invention may be used to detect changes in the refractive index of probe and, thereby characterize the nature of chemical or physical interaction of target chemical species and an interacting species.

In an exemplary embodiment, the SPR sensor generates at least one reference measurement corresponding to the refractive index of the probe region prior to introduction of interacting species. Interacting species are introduced into the reactor and permitted to interact with the target species in the probe region. The SPR sensor generates at least one analytical measurement, which is compared to the reference measurement to detect a change in the refractive index of said probe region. In an exemplary embodiment, analytical measurements are repeatedly acquired and compared to each other to characterize changes in refractive index as a function of time. Such changes may be related to the chemical and physical nature of the interaction between interacting species and target species. Exemplary methods of the present invention are capable of determining binding affinities, rate constants, equilibrium constants and thermodynamic parameters that characterize the interaction between target species and interacting species.

The SPR sensing and imaging methods and devices of the present invention are broadly applicable for detecting and characterizing virtually any material capable of changing the refractive index. In particular, the present methods are particularly useful for detecting chemical species including, but not limited to, biological polymers, such as proteins, peptides, oligonucelotides, glycoproteins, DNA, RNA, polysaccharides, and lipids and aggregates thereof. An advantage of the present methods and devices is that they provide sensitive detection methods which do not require pre-detection chemical labeling processes which are time consuming, costly and may substantially affect the chemical and/or physical properties of the labeled chemical species. Other advantages of the present sensing and imaging methods is that they provide very high time resolution, high sensitivity up to about 100 fM and require very low sample volumes.

The present invention provides methods and devices broadly applicable to any measurement technique or other processes which involves the formation of SPs. Particularly, wavelength tunability of the devices of the present invention provides efficient SP excitation. For example, wavelength tunable SP devices of the present invention may be used for effective excitation of photoluminescent materials in the SPR probe region. In an exemplary embodiment, devices of the present invention are used to generate SPs capable of exciting fluorescent or phosphorescent transitions of chemical species in the probe region, particularly in chemical species bound to the probe region. These devices may include a second detector positioned in optical communication with such fluorescent materials, which is capable of quantifying the intensity of SP induced fluorescence. Alternatively, wavelength tunable SP devices of the present invention may provide a means of delivering energy to materials in a reaction region to induce chemical or physical changes in the material.

In another aspect, the present invention provides a method of sensing the refractive index of a probe region comprising the steps of: (i) passing light from a polychromatic light source through a polarizer, thereby generating light propagating along an incident light propagation axis; (ii) directing said light onto an optical assembly comprising a dielectric layer, a sample dielectric layer and a conducting layer positioned between the dielectric layer and the dielectric sample layer, thereby generating light propagating along a reflected light propagation axis, wherein a portion of said dielectric sample layer adjacent to said conducting layer comprises the probe region; (iii) passing said light through a selectably adjustable wavelength selector positioned in the optical path between said light source and a detector; (iv) detecting said light with said detector, thereby sensing the refractive index of the probe region, and (v) adjusting said selectably adjustable wavelength selector to transmit light having a distribution of wavelengths selected to generate surface plasmons on a surface of said conducting layer in contact with said dielectric sample layer.

In another aspect, the present invention provides a method of generating an image of a probe region comprising the steps of: (i) passing light from a polychromatic light source through a polarizer, thereby generating light propagating along an incident light propagation axis; (ii) directing said light onto an optical assembly comprising a dielectric layer, a sample dielectric layer and a conducting layer positioned between a dielectric layer and dielectric sample layer, thereby generating light propagating along a reflected light propagation axis, wherein a portion of said dielectric sample layer adjacent to said conducting layer comprises the probe region; (iii) passing said light through a selectably adjustable wavelength selector positioned in the optical path between said light source and a detector; (iv)detecting said light with said detector, thereby generating said image of said probe region, and (vi) adjusting said selectably adjustable wavelength selector to transmit light having a distribution of wavelengths selected to generate surface plasmons on a surface of said conducting layer in contact with said dielectric sample layer.

In another aspect, the present invention provides a method of detecting a change in the refractive index of a probe region comprising the steps of: (i) passing light from a polychromatic light source through a polarizer, thereby generating light propagating along an incident light propagation axis; (ii) directing said light onto an optical assembly comprising a dielectric layer, a sample dielectric layer and a conducting layer positioned between a dielectric layer and dielectric sample layer, thereby generating light propagating along a reflected light propagation axis, wherein a portion of said dielectric sample layer adjacent to said conducting layer comprises the probe region; (iii) passing said light through a selectably adjustable wavelength selector positioned in the optical path between said light source and a detector, wherein said selectably adjustable wavelength selector is adjusted to transmit incident light having a distribution of wavelengths selected to generate surface plasmons on a surface of said conducting layer in contact with said dielectric sample layer; (iv) detecting said light with said detector, thereby generating at least one reference measurement, (v) detecting said light with said detector, thereby generating at least one analytical measurement, and (vi) comparing said reference measurement and said analytical measurement to detect said change in the refractive index of said probe region.

BRIEF DESCRIPTION OF THE DRAWINGS

As illustrated in FIG. 3, the optical interference filter is selectably rotatable about a rotation axis which is orthogonal to the plane of incidence.

FIG. 12 shows a series of images taken of a thiol and water patterns with an optical interference filter positioned a several different tilt angles.

FIGS. 13A and B shows images of thiol patterns with minimum feature sizes of approximately 100 µm (FIG. 13A, left side) and approximately 50 µm (FIG. 13B, right side) generated by an exemplary SPR senor of the present invention.

FIG. 14B shows an image of the same region of the reactor with a 2 mg ml$^{-1}$ solution of BSA in phosphate buffered saline (PBS). FIG. 14C shows an image of the same region with a background of water after pumping water through the reactor to remove all unbound protein. FIG. 14D shows a difference image resulting from subtraction of images in FIG. 14A and FIG. 14C.

DETAILED DESCRIPTION OF THE INVENTION

Figure 1:
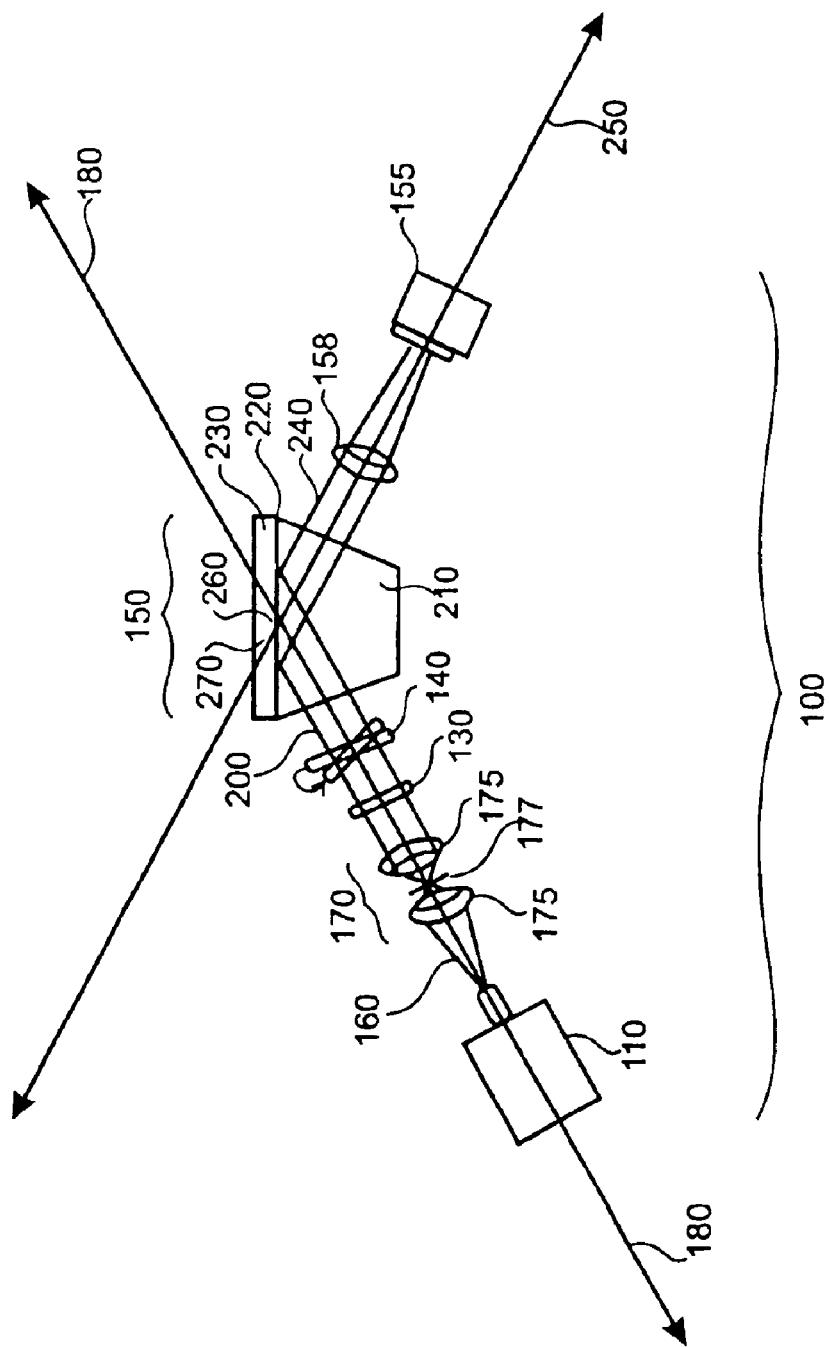
FIG. 1 is a schematic drawing showing a side plan view of a SPR imaging device of the present invention having a selectably adjustable wavelength selector positioned between the polychromatic light source and the SPR optical assembly.

Referring to the drawings, like numerals indicate like elements and the same number appearing in more than one drawing refers to the same element. In addition, hereinafter, the following definitions apply:

"Chemical species" refers generally and broadly to a collection of one or more atoms, molecules and/or macromolecules whether neutral or ionized. In particular, reference to chemical species in the present invention includes but is not limited to biopolymers. Chemical species in a liquid sample may be present in a variety of forms including acidic, basic, molecular, ionic, complexed and solvated forms. Chemical species also includes non-covalently bound aggregates of molecules. Chemical species includes biological molecules, i.e. molecules from biological sources, including biological polymers, any or all of which may be in the forms listed above or present as aggregates of two or more molecules.

"Distribution of transmitted wavelengths" refers to a two-dimensional distribution of the intensities of light of different wavelengths transmitted by a wavelength selector, such as an optical interference filter, monochromator or spectrometer. A distribution of transmitted wavelengths may be characterized in terms of center wavelength, bandwidth and intensity profile of transmitted wavelengths. In the present invention, the distribution of transmitted wavelengths of light detected by a detector is determined by the combination of the optical properties of the light source and the selectably adjustable wavelength selector. In an exemplary embodiment, the distribution of transmitted wavelengths of light directed on an SPR optical assembly and/or detected by a detector has a substantially Gaussian intensity profile and center wavelength corresponding to the wavelength of light having the largest intensity. Wavelength tunable SPR sensors and imaging devices of the present invention provide excitation light and/or detected light having a selectably adjustable distribution of transmitted wavelengths.

"Center wavelength" is a characteristic of a distribution of transmitted wavelengths of light. In some embodiments, center wavelength refers to the midpoint wavelength in a distribution of transmitted wavelengths. In other embodiments, the center frequency refers to the transmitted wavelength in a distribution of wavelength having the largest intensity. In other embodiments, center wavelength refers to the average wavelength in a distribution of transmitted wavelengths. The center wavelength typically corresponds to the wavelength in a distribution of transmitted wavelength having the largest intensity for wavelength distributions having Gaussian or Lorentizian intensity profile.

"Light source" refers to any device or material capable of generating electromagnetic radiation or a plurality of devices or materials capable of generating electromagnetic radiation. Preferred light sources in the present invention are capable of generating light in the near infrared region of the electromagnetic spectrum (about 800 nm to about 1200 nm). In an exemplary embodiment useful for avoiding optical interference affects in SPR imaging and sensing applications, a light source of the present invention generates incoherent light. Light sources useable in the methods and devices of the present invention include halogen lamps, light emitting diodes, fluorescent lamps, tungsten-filament lamps, grey body light sources and black body light sources.

"Bandwidth" refers to a characteristic of a distribution of transmitted wavelengths of light. Bandwidth may be defined in terms of the full width at half maximum of an intensity profile of a distribution of transmitted wavelengths, which refers to the full width at an transmittance equal to one half of the maximum transmittance. In exemplary embodiments of the present invention bandwidth of detected light is primarily determined by the transmission properties of a selectably adjustable wavelength selector, such as optical interference filter. The transmission bands of exemplary selectably adjustable wavelength selectors of the present invention are selected over the range of about 1 nm to about 100 nm and more preferably 1 to about 20 nm in some embodiments. Use of wavelength selectors capable of providing a distribution of transmitted wavelengths characterized by a large bandwidth (>10 nm) is useful in some embodiments for increasing signal-to-noise ratio.

"Conducting layer" refers to a layer comprising a conductor material, such as a metal, or a semiconductor material. Conducting layers support the formation of surface plasmons and are used as sensing surfaces in the present invention. Preferred conducting layers in the present invention are thin (<50 nm) gold or silver layers.

"Dielectric sample layer" refers to a dielectric layer positioned adjacent to the surface of a conducting layer having surface plasmons thereon. Dielectric sample layers of the present invention include probe regions close to the sensing surface of a conducting layer. Probe regions of the present invention comprise a volume adjacent to the surface of a conducting layer having surface plasmons thereon (a sensing surface) having a depth that is defined by the decay length of the surface plasmons into the dielectric sample layer. SPR sensors and imaging devices of the present invention are capable of sensing, monitoring and characterizing changes in the refractive index of a probe region. Dielectric sample layers and probe regions may be operational connected to flow cells and/or flow reactors for introduction of material to the dielectric sample layer and/or probe region. In these embodiments, selection of the flow conditions of the flow cell or flow reactor may adjust the composition of the dielectric sample layer and the probe region. Alternatively, dielectric sample layers and probe regions may be operational connected to static cells and/or static reactors.

"Selectably adjustable wavelength selector" refers to a device, device component or combination of optical components capable of selecting the distribution of wavelengths of light which are transmitted through the wavelength selector. "Selectably adjustable wavelength selector" also refers to a device, device component or combination of optical components capable of selecting the distribution of wavelengths of light which are substantially prevented from transmitting through the wavelength selector. Selectably adjustable wavelength selectors of the present invention may transmit a distribution of transmitted wavelengths characterized by a center wavelength, bandwidth and intensity profile. Exemplary selectably adjustable wavelength selectors of the present invention include, but are not limited to, optical interference filters, etalons, Fabry-Perot etalons, fiber optic interferometric filters, fiber optic devices, fiber Fabry-Perot filters, monochromators, spectrometers, gratings and/or prisms, slits or any combinations thereof. Exemplary optical interference filters of the present invention are capable of selectably adjusting the distribution of transmitted wavelengths by rotation about a rotational axis which is oriented orthogonal to an incident or reflected beam axis.

"Surface plasmon resonance sensor" or "SPR sensor" are used synonymously and refer to any device or device component capable of monitoring, detecting or characterizing changes in the refractive index of a probe region using excitation of surface plasmons. In an exemplary embodiment, SPR sensors detect changes in the refractive index of a probe region located proximate to a sensing surface having surface plasmons localized thereon. Exemplary SPR sensors comprise SPR imaging devices which are capable of generating an image of a probe region corresponding to refractive indices and/or composition of the probe region. Alternatively, SPR sensors of the present invention generate surface plasmons capable of exciting photoluminescent materials positioned proximate to one or more surfaces of a conducting layer.

"SPR optical assembly" refers to any combination of optical components which are capable of coupling radiant energy into surface plasmons. In an exemplary embodiment, a SPR optical assembly of the present invention comprises a dielectric layer, a dielectric sample layer and conducting layer arrange in the Kretschmann optical configuration or Otto optical configuration. Alternatively, SPR optical assemblies may comprise waveguides, fiber optic devices or diffraction gratings. SPR optical assemblies of the present invention may include a number of optical components including, but not limited to, prisms, thin gold films, thin silver films, thin semiconductor films, flow reactors, static reactors, microfluidic devices, fluid channels, optical alignment systems, rotational stages or any combination of these components.

"Tilt angle" is a characteristic of rotational position. In exemplary embodiments, tilt angle refers to rotational orientations of an optical interference filter relative to normal incidence with respect to the incident light propagation axis or reflected light propagation axis. Specifically, tilt angle refers to the angular deviation of the surface of a rotated optical component, such as an optical interference filter, as measured relative to the incident light propagation axis or reflected light propagation axis. Exemplary surfaces of optical interference filters of the present invention may be oriented at tilt angles ranging from 0° to about 60°, more preferably from 0° to about 35°

In the following description, numerous specific details of the devices, device components and methods of the present invention are set forth in order to provide a thorough explanation of the precise nature of the invention. It will be apparent, however, to those of skill in the art that the invention can be practiced without these specific details.

This invention provides methods, devices and device components for sensing changes in the refractive index and composition of a probe region proximate to a sensing surface. In particular, wavelength tunable SPR sensing devices and images devices are provided which are capable of detecting SPR conditions and generating SP resonance curves at a constant angle of incidence. Further, the present invention provides methods and devices of generating SPR images of a probe region in a sample dielectric layer.

FIG. 1 schematically illustrates a side plan view of a SPR imaging device of the present invention having a selectably adjustable wavelength selector positioned between a polychromatic light source and a SPR optical assembly. The exemplary SPR imaging device 100 comprises a polychromatic light source 110 in optical communication with polarizer 130, optical interference filter 140, SPR optical assembly 150 and two-dimensional detector 155. As shown in FIG. 1, exemplary SPR imaging device 100 may optionally include light collimation element 170 comprising lenses 175 and pin hole 177 positioned between light source 110 and polarizer 130. Further, SPR imaging device may optional comprise collecting and imaging optical element 158 positioned between optical assembly 150 and detector 155.

Incident light 160 from optical source 110 is collimated by collimation element 170 and propagates along incident light propagation axis 180. Incident light 160 is passed through polarizer 130 positioned to intersect light propagation axis 180, which is capable of selecting the polarization state of incident light 160. Polarizer 130 is preferably capable of selected substantially p-polarized or s-polarized orientations of incident light 160 and also of rapidly switching between selected p-polarization and s-polarization orientations. A selected distribution of transmitted wavelengths of polarized incident light 160 passes through optical interference filter 140, which is positioned to intersect light propagation axis 180. In the embodiment illustrated in FIG. 1, optical interference filter 140 is selectably rotatable about a rotational axis which is oriented orthogonal to the incident light propagation axis 180 (due to the perspective of FIG. 1, the rotational axis of optical interference filter 140 is not shown but is oriented such that it comes out of the plane of the drawing). Two different rotational orientations of optical interference filter 140 are shown in FIG. 1. In this embodiment, the wavelength distribution of transmitted light may be selectably adjusted by rotation of optical interference filter 140. In a preferred embodiment, optical interference filter 140 is mounted on a rotation stage (not shown in FIG. 1) so that the angle of the filter face with respect to the incident light propagation axis may be selectively varied, thus, varying the wavelengths of light that are passed by the filter. Therefore, the rotational position of optical interference filter 140 determines the wavelength distribution of light which is directed to optical assembly 150 and subsequently detected by detector 155

Light having a selected wavelength 200 is directed onto SPR optical assembly 150, which comprises a prism 210, a thin conducting layer 220, and a dielectric sample layer 230 arranged in the Kretschmann optical configuration. A preferred thin conducting layer 220 of the present invention are gold or silver layers having a thickness ranging from about 30 nm to about 60 nm. A preferred dielectric sample layer 230 comprises a probe region 270 operationally coupled to a reactor or cell, such as a flow cell, static cell, flow cell reactor or static cell reactor, capable of introducing material into a probe region 270 proximate to the surface of thin conducting layer 220. Illumination of the SPR optical assembly 150 at angles of incidence resulting in total internal reflection generates light 240 propagating along a reflected light propagation axis 250 that is detected by two-dimensional detector 155. Optionally, light from optical assembly 150 may be collected by optical collection and focusing element 158 prior to detection to enhance detection sensitivity and resolution.

At least a portion of light having wavelengths that satisfy the SPR resonance condition is not reflected by optical assembly 150. Rather, this radiant energy is converted into SPs on sensing surface 260, which comprises the surface of conducting layer 220 in contact with dielectric sample layer 230. The resonance condition controlling conversion of radiant energy to surface plasmons is strongly dependent on the refractive index of a probe region 270 proximate to the sensing surface 260. Detection of light reflected by optical assembly 150 to detector 155 is capable of characterizing which wavelengths of light are converted to SPs and the extent of this process. As shown in FIG. 1, preferred optical geometries of SPR sensors and imaging devices of the present invention have a constant angle of incidence selected to generate total internal reflection of the incident beam upon illumination of the SPR optical assembly. The present invention also includes, however, embodiments wherein the angle of incidence is selectably adjustable. These embodiments correspond to SPR sensors and imaging devices that are both angle and wavelength tunable.

Figure 2:
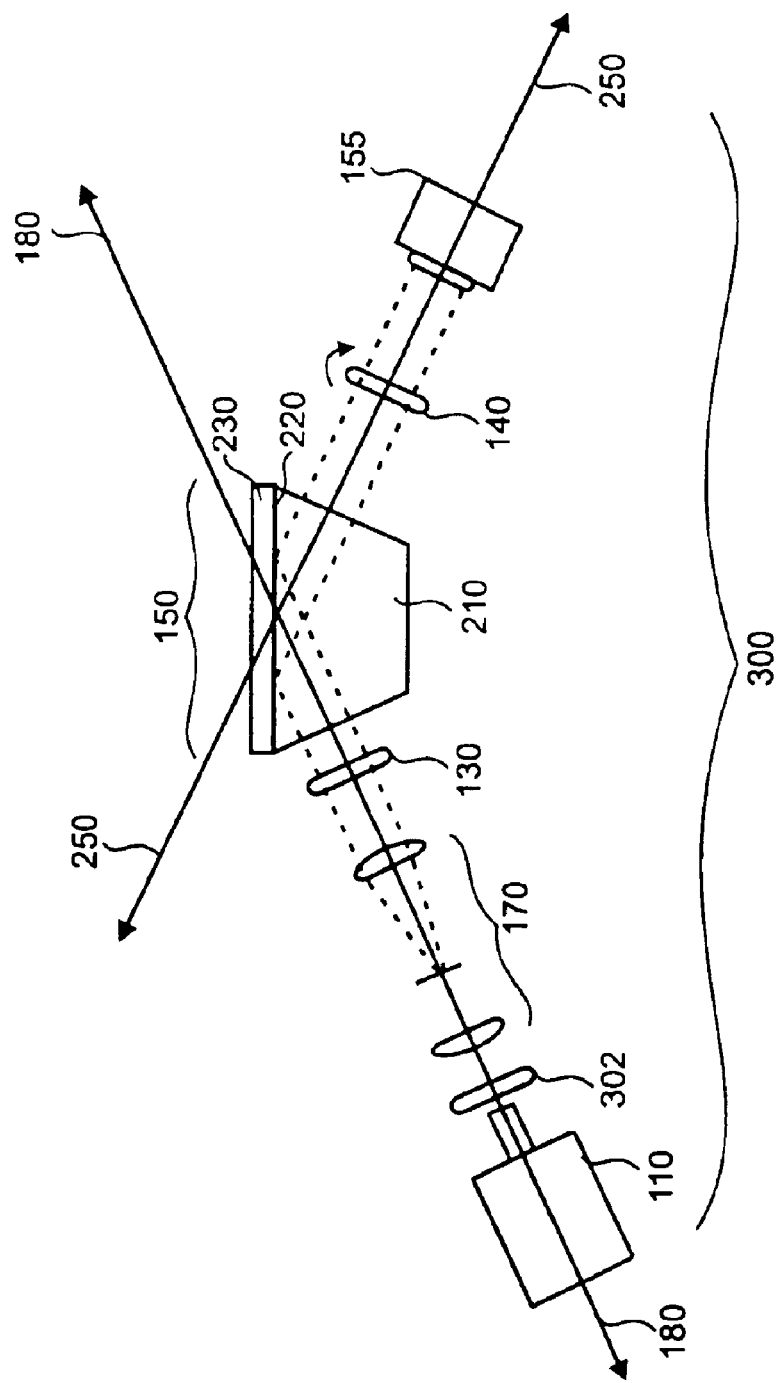
FIG. 2 is a schematic drawing showing a side plan view of a SPR imaging device of the present invention having a selectably adjustable wavelength selector positioned between the SPR optical assembly and the detector.

FIG. 2 shows an exemplary SPR imaging device 300 having an alternative optical configuration. In this optical configuration, optical interference filter 140 is positioned to intersect reflected light optical propagation axis 250. Similar to the optical configuration shown in FIG. 1, optical interference filter is selectably rotatable about a rotational axis. In exemplary SPR imaging device 300, optical interference filter 140 is selectably rotatable about a rotational axis that is oriented orthogonal to the reflected light propagation axis 250 (due to the perspective of FIG. 2, the rotational axis of optical interference filter 140 is not shown but is oriented such that it comes out of the plane of the drawing). In this embodiment, the wavelength distribution of transmitted light may be selectably adjusted by rotation of optical interference filter 140. Only one rotational orientation of optical interference filter 140 is shown in FIG. 2. In an exemplary embodiment, optical interference filter 140 is mounted on a rotation stage (not shown in FIG. 2) so that the angle of the filter face with respect to the reflected light propagation axis may be selectively varied, thus, varying the wavelengths of light that are passed by the filter. Therefore, the rotational position of optical interference filter 140 determines the wavelength distribution of light detected by detector 155. As shown in FIG. 2, SPR imaging device 300 may optionally include cutoff filter 302 positioned between light source 110 and optical assembly 150. In an exemplary embodiment cutoff filter 302 is a 700 nm long pass filter and/or a 1000 nm short pass filter, which reduces the intensity of light having wavelengths less than 700 nm to minimize heating of optical assembly 150 by incident light.

To generate a SPR image, polarizer 130 is adjusted to transmit p-polarized light and optical interference filter 140 is adjusted to transmit light having a distribution of wavelengths satisfying the SP resonance condition for a particular probe region composition and refractive index. Detector 155 detects light reflected from optical assembly 150, thereby generating a first two-dimensional distribution of reflected light intensities corresponding to p-polarized light. In some embodiments, the two-dimensional distribution of reflected p-polarized light provides a SPR image of the probe region. Use of a combination of light source and wavelength selector having intensities which vary with wavelength often requires normalization of the measured p-polarized reflected light intensities in order to calculate an image in terms of percent reflectivity. To convert the reflected intensities corresponding to p-polarized light into percent reflectivities, polarizer 130 is adjusted to transmit s-polarized light and a second two-dimensional distribution of reflected light intensities is generated corresponding to s-polarized light. An image of the probe region in terms of percent reflectivity is generated by taking the ratio of p-polarized intensity to s-polarized intensity at each pixel location.

At larger filter rotation angles, the polarization-dependent transmission effects of the interference filter become significant. Specifically, the intensity of transmitted s-polarized light decreases and the center wavelength is shifted to shorter wavelengths as compared to the transmitted p-polarized light through the same interference filter. As a result, at larger filter rotation angles, normalized images must include a correction factor for this effect. The correction factor for any imaging angle can be simply determined by measuring the intensities of p-polarized and s-polarized light passed by the filter in the absence of surface plasmon generation. The ratio (intensity p-polarized)/(intensity s-polarized) itself can be used to correct for polarization-dependent transmission effects of the interference filter. For example, each measured percent reflectivity value may be divided by the ratio of the intensity of p-polarized light to the intensity of s-polarized light corresponding to the center wavelength of the transmitted light distribution to correct for polarization dependent transmission affects. In one embodiment, (the intensity p-polarized)/(intensity s-polarized) correction factor is measured at several different imaging angles and the data is fit by a third order polynomial function to generate a correction curve for the system. The correction curve is then used to obtain the correction factor for any distribution of transmitted wavelengths.

Figure 3:
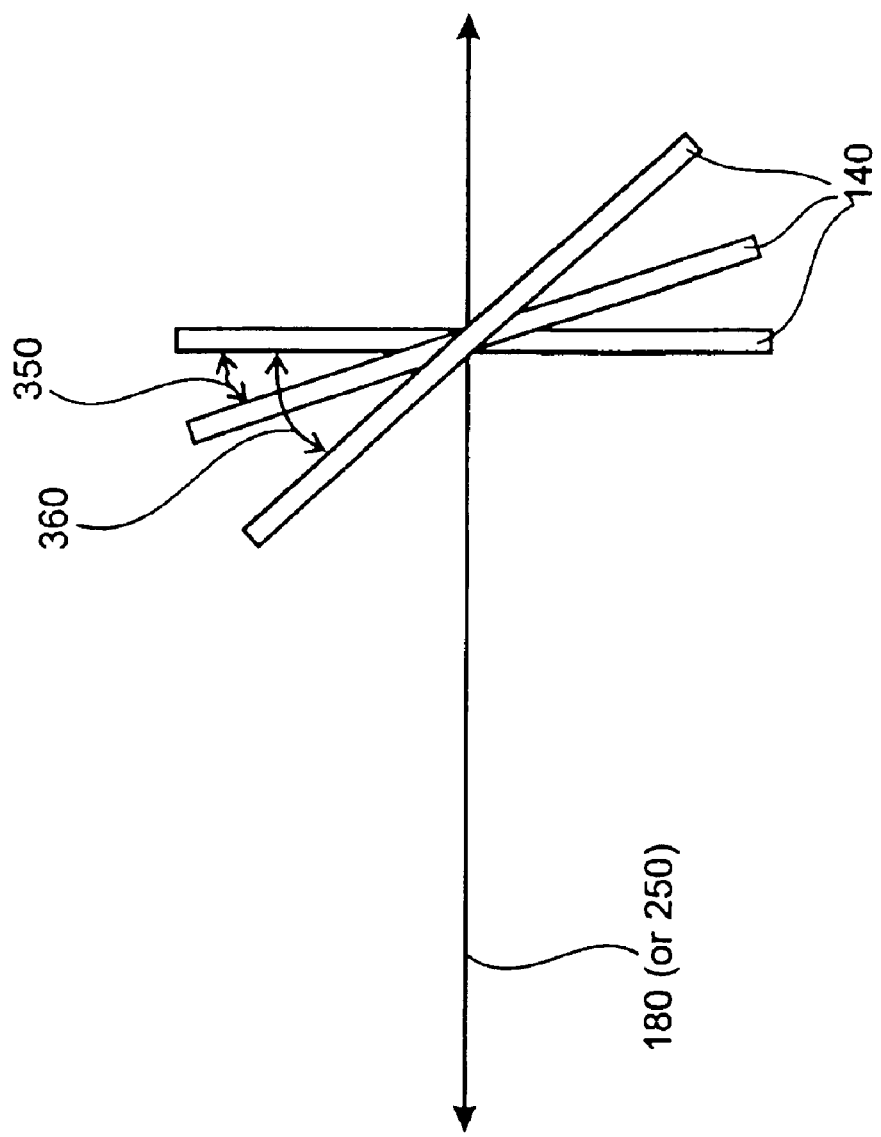
FIG. 3 is a schematic drawing showing a side plan view of an exemplary selectably adjustable wavelength selector comprising an optical interference filter.

FIG. 3 is an expanded view of optical interference filter 140 showing a plurality of rotational orientations relative to normal incidence with respect to incident light propagation axis 180 or reflected light propagation axis 250. Specifically, rotation orientations corresponding to a first tilt angle 350 and a second tilt angle 360 are shown. First tilt angle 350 is smaller than second tilt angle 360. As shown in FIG. 3, in the context of some embodiments of the present invention, tilt angle refers to angular deviation as measured relative to an angular orientation of optical interference filter such that it is orthogonal to the incident light propagation axis or reflected light propagation axis. Alternatively expressed, tilt angle is 90 degrees minus the angle between the normal to the plane defined by the filter face and the incident beam axis. In an exemplary embodiment, the optical interference filter transmits light having a distribution of wavelengths that is characterized by a center wavelength, bandwidth and wavelength intensity profile. Preferred bandwidths range form about 1 nm to about 30 nm and preferred wavelength intensities profiles are substantially Gaussian shaped or Lorentzian shaped. Exemplary optical interference filters provide center frequencies which are tunable over a range of about 60 nm and more preferably about 100 nm.

In one embodiment, rotation of optical filter 140 shifts the center wavelength of the distribution of transmitted wavelengths to shorter wavelengths. In an exemplary embodiment wherein the optical interference filter comprises a Fabry-Perot etalon, the center wavelength of the optical interference filter is provided by the expression:

$$\lambda_{center}(\theta_{tilt}) = (\lambda_{center}(0))\left(1 - \left(\frac{\sin^2\theta_{tilt}}{n^2}\right)\right)^{0.5}; \qquad (VI)$$

wherein $\lambda_{center}$ is the center wavelength of the distribution of transmitted wavelengths, $\theta_{tilt}$ is the tilt angle, $\lambda_{center}(0)$ is the center wavelength at normal incidence with respect to the reflected or incident light propagation axes and n is the refractive index of the optical interference filter. For optical interference filters comprising Fabry-Perot etalons n is the half wavelength thick layer of the filter.

Figure 4:
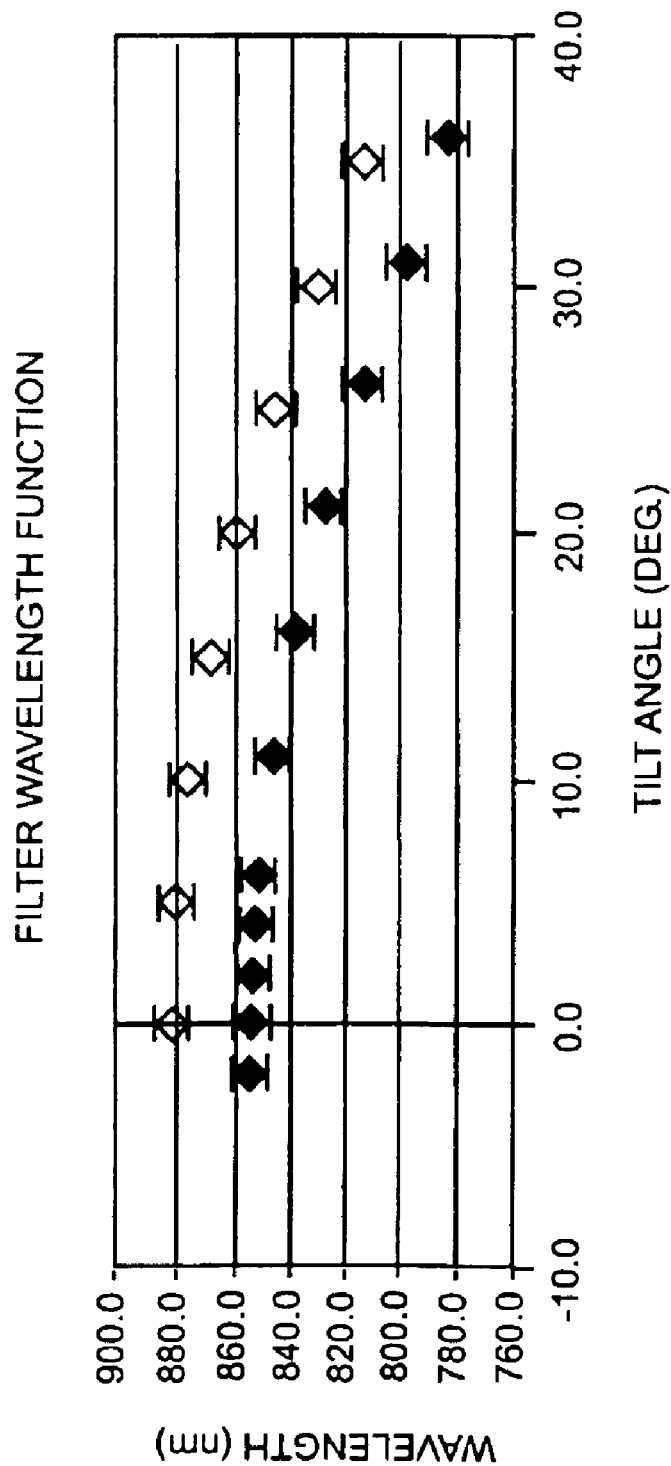
FIG. 4 is a plot of center wavelength as a function of tilt angle for two interference filters having center wavelengths at normal incidence of about 850 nm (filled diamonds) and about 880 nm (open diamonds).

An exemplary optical interference filter useable in SPR sensors and imaging devices of the present invention has a full width at half maximum bandwidth of about 10 nm at a normal incidence (angle between the normal to the filter face and the incident light axis). FIG. 4 show a plot of center wavelength as a function of tilt angle for two interference filters having center wavelengths at normal incidence of about 850 nm (filled diamonds) and about 880 nm (open diamonds). As shown in FIG. 4, the center wavelengths passed by the filters shift by about 65 nm for a variation in tilt angle from 0 to 35°. The variation of the center wavelength agreed with the values predicted using Equation VI. The intensity distribution of wavelengths remained substantially Gaussian up to tilt angles of about 35°. The width of the Gaussian intensity profiles, however, increases by approximately 4% as the filter is titled from 0° to about 20°. Above a tilt angle of about 20°, the width of the intensity distribution increases more rapidly with angle, up to an additional 20%.

The range in wavelength tuning needed to optimally image samples that vary in refractive index from about $5 \times 10^{-5}$ to about $3 \times 10^{-3}$ from a baseline of water on bare Au (refractive index equal to 1.328 at ~850 nm) was estimated using a 3-layer SPR model. The results of these calculations indicate that the optimal range of wavelengths is from about 845 nm to about 857 nm for characterizing the expected change in SP resonant wavelength. This range spans less than 15 nm and, thus, is easily covered by the wavelength shift range provide by a single optical interference filter.

SPR sensors and imaging devices of the present invention may comprise stand-alone instruments. Alternatively, the SPR sensors and imaging devices of the present invention may be integrated into other devices or used as device components in instruments. The sensors of the present invention may be coupled to reactors, flow cells, static cells, flow cell reactors, static reactors, microfluidic devices, biological system analyzers, instruments for characterizing the interactions between molecules, and drug screening instruments. Flow cells operationally coupled to the sensors and imaging devices of the present invention are useful for delivering chemical species to the probe region. For example, the SPR sensors of the present invention may be combined with a microfluidic fluid delivery device to introduce materials into the probe region. In an exemplary embodiment, the sensing surface of a sensor of the present invention comprises one wall of a microfluidic flow cell. SPR sensing measurements may be conducted during conditions of continuous liquid flow over the surface or static flow conditions. Use of a microfluidic flow system is beneficial because it provides precise control over the time-point and duration of sample delivery to the probe region.

All references cited in this application are hereby incorporated in their entireties by reference herein to the extent that they are not inconsistent with the disclosure in this application. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques specifically described herein are intended to be encompassed by this invention.

EXAMPLE 1

Characterization of an Exemplary SPR Sensor

The ability of SPR sensors of the present invention to sense changes in the refractive index of a probe region was verified by experimental and computational studies. Specifically, it is a goal of the present invention to provide SPR sensors capable of sensitively detection and characterization changes in the refractive index of a probe region. Further, it is a goal of the present invention to SPR sensors providing a large dynamic range, which are capable of probing materials having a wide range of refractive indices.

Figure 5:
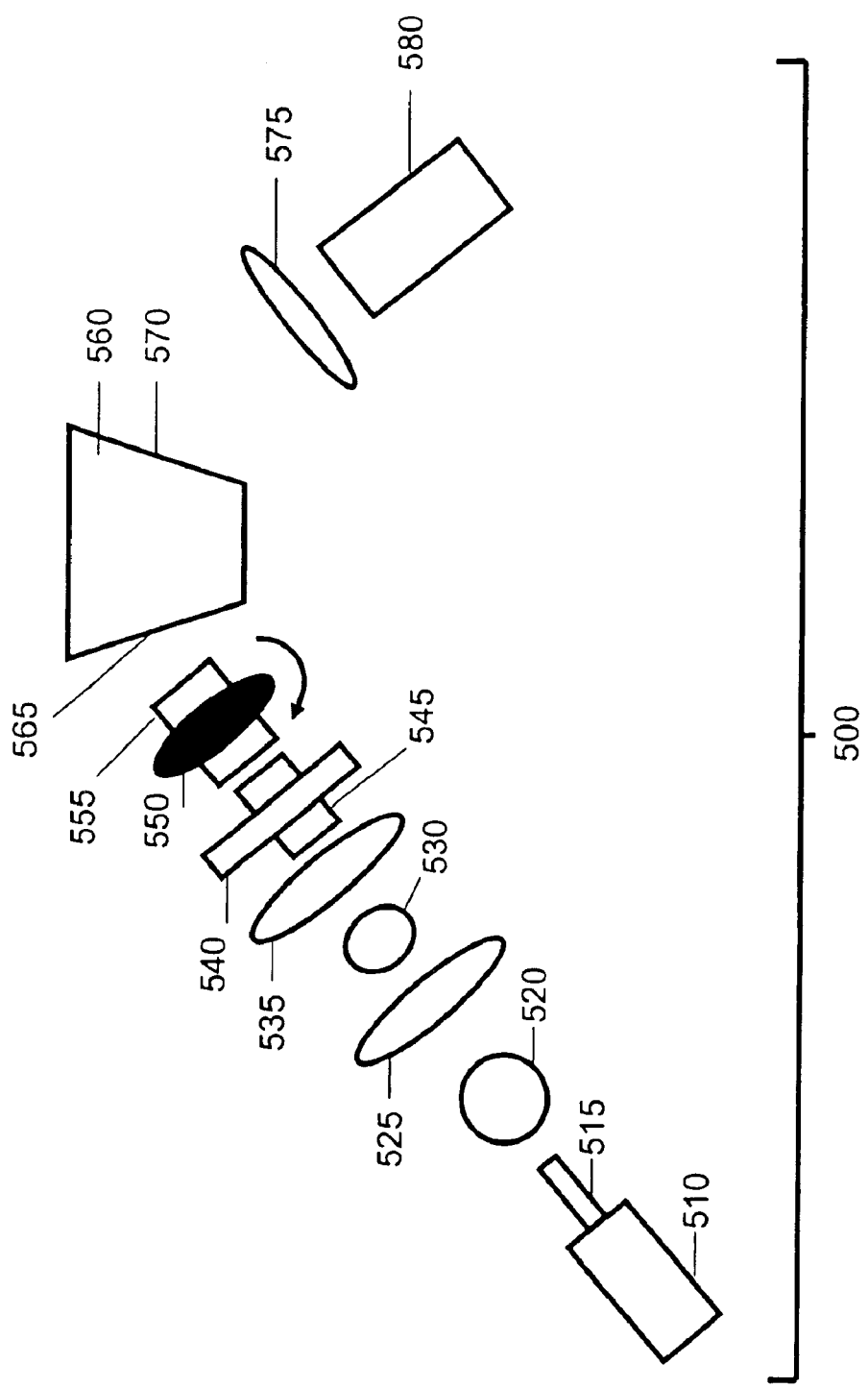
FIG. 5 is a schematic diagram illustrating a top plane view of an exemplary SPR imaging device based on the Kretschmann SPR configuration.

To achieve the aforementioned goals, detection sensitivities and dynamic ranges of an exemplary SPR sensor were computationally modeled and evaluated by monitoring the refractive indices of low concentration sucrose solutions. The exemplary SPR sensor 500 employed in these studies is based on the Kretschmann configuration and is shown in FIG. 5. The polychromatic light source is a 150 W quartz halogen lamp 510 (Dolan-Jenner, Lawrence, Mass.) coupled to a multi-fiber light pipe 515 (Edmund Industrial Optics, Barrington, N.J.). Light from the source passes through iris 520 and is collected by an achromatic lens 525 (Edmund Industrial Optics, Barrington, N.J.) and focused at a pinhole 530 (100 μm in diameter, Edmund Industrial Optics, Barrington, N.J.). A second achromatic lens 535 (Edmund Industrial Optics, Barrington, N.J.) collects light from the pinhole 525 and forms a collimated beam. This expanded and collimated beam passes through a polarizer 540 (Edmund Industrial Optics, Barrington, N.J.). The polarizer is mounted onto a motorized rotation stage 545 (Newport Corporation, Irvine, Calif.) so p-polarized and s-polarized images can be acquired conveniently. The light then passes through an interference filter 550 (Edmund Industrial Optics, Barrington, N.J.) that selects a narrow band (10 nm FWHM) of operating wavelengths in the near infrared to optimally contrast the range of refractive indexes in the sample. The filter is mounted onto a motorized rotation stage 555 (Newport Corporation, Irvine, Calif.) so that the angle of the filter face with respect to the collimated source beam may be varied, thus varying the wavelengths of light that are passed by the filter. Rotation of the filter over tilt angles of about 35° form normal incidence, results in variation of the wavelengths passed by the filter by ~70 nm toward shorter wavelengths.

The SPR optical assembly 560 comprises a prism, thin gold film and a flow reactor. The entrance and exit surfaces 565 and 570 of the prism were custom-ground (Matthew's Optical, Poulsbo, Wash.) to be perpendicular to the source beam for an incident angle of 64.8° at the metal surface. Light reflected form the SPR optical assembly passes through an imaging lens 575 (Edmund Industrial Optics, Barrington, N.J.) to form a focused image (magnification<1) at the CCD detector 580 (Retiga EX, QImaging, Burnaby, Canada). The area of sample interrogation is circular and ~16 mm in diameter. Data acquisition is performed with software written in-house using Labview 6.1 (National Instruments, Austin, Tex.).

Use of a light source and interference filter combination providing incident light intensities that vary with center wavelength requires normalization of the p-polarized signal by the s-polarized signal. Further, polarization-dependent transmission effects of the interference filter become significant at larger filter rotation angles. As compared to transmitted p-polarized light, the intensity of transmitted s-polarized light decreases and the center wavelength is shifted to shorter wavelengths as tilt angle is increased. As a result, at larger filter rotation angles, normalized images must include a correction factor for this effect. Correction factors were determined by measuring the intensities of p-polarized and s-polarized light passed by the optical interference filter in the absence of surface plasmon formation. The ratio (intensity p-polarized)/(intensity s-polarized) itself was used to correct for polarization-dependent transmission effects of the interference filter. Each measured percent reflectivity value was divided by the correction factor to correct for polarization dependent transmission affects.

Figure 6:
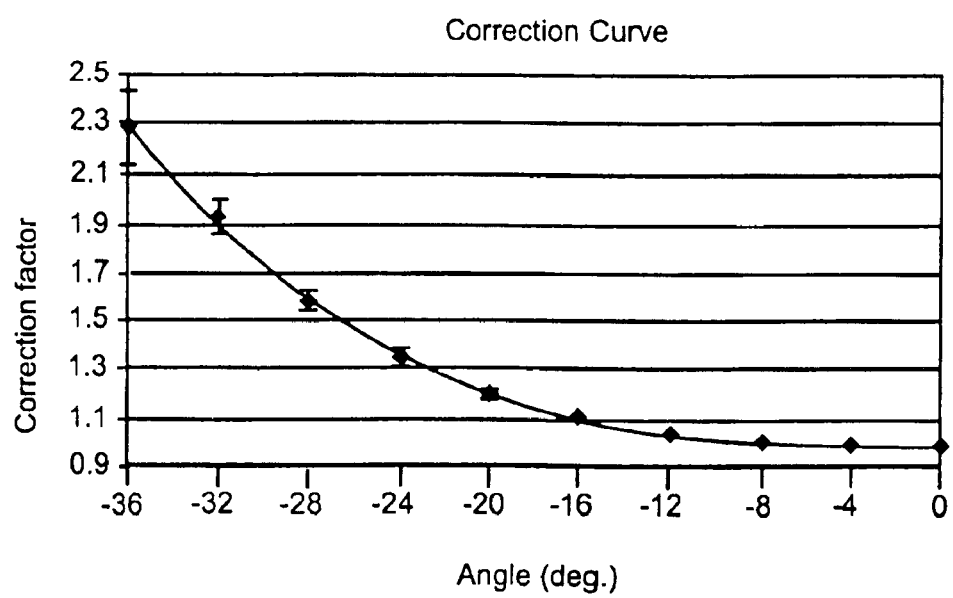
FIG. 6 is a correction curve for correcting acquired SPR images for polarization dependent transmission of light through an optical interference filter.

FIG. 6 is a correction curve for correcting acquired SPR images for polarization dependent transmission of light through the interference filter. The diamond data points in FIG. 6 show the sum of the intensity of p-polarized light divided by the sum of the intensity of s-polarized light for ten different filter rotation angles in the absence of surface plasmons. To estimate the variability in the correction procedure, data was taken from five different regions of the source beam. Each point in the plot shown in FIG. 6 is the average of 400 pixels. The error in the data points increases with increasing filter tilt angle, from ≦1% for rotation angles less than 24° to 6% at an angle of 36°. The variation between different runs is considerably smaller, ≦0.6% for all filter tilt angles. Also, shown in FIG. 6 is the correction curve, a $3^{rd}$ order polynomial, obtained from the data. As is apparent from the plot, the correction factor at rotation angles of less than 25° is small (less than 1.3) but increases rapidly for the larger rotation angles, up to 2.3 at 36°.

Figure 7:
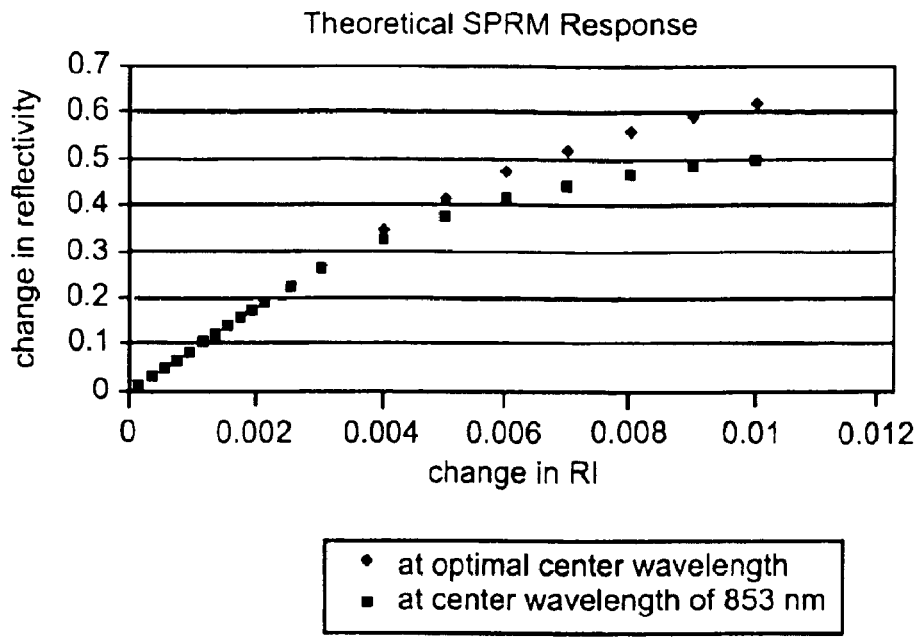
FIG. 7 is the expected response of an exemplary SPR imaging device for changes in sample refractive index.
Figure 8:
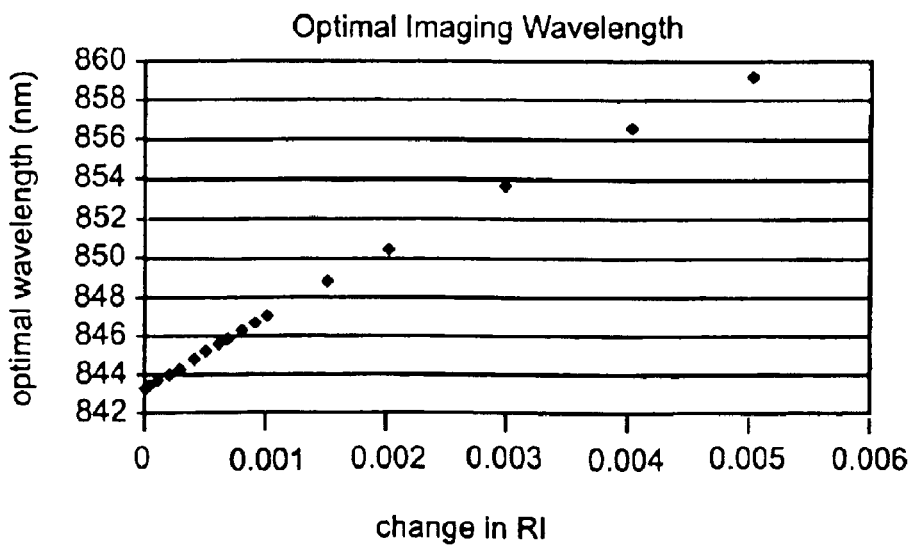
FIG. 8 shows the optimal center imaging wavelength as a function of change in refractive index from a base refractive index of water.

Using a 3-layer Fresnel model, the predicted response of an exemplary SPR sensor was calculated for a probe region refractive index that spans 4 orders of magnitude, $1 \times 10^{-6}$ to $1 \times 10^{-2}$. The calculations assumed a base refractive index of water equal to 1.328 at ~850 nm. The expected response of the SPR sensor for changes in sample refractive index is shown in FIG. 7. The data shown in FIG. 7 takes into account the experimentally measured transmission band of our filter equal to about 10 nm. Each diamond data point corresponds to the expected response of the instrument for a given change in sample refractive index at the optimal center imaging wavelength for that sample change in refractive index. The square data points correspond to the expected response of the instrument at a single center wavelength setting of 853 nm. The SPR sensor is expected to have a linear response up to a change in refractive index of ~$3 \times 10^{-3}$ (for comparison, the adsorption of a monolayer of the protein bovine serum albumin onto the Au surface corresponds to a refractive index change of ~$1 \times 10^{-3}$). Also of note is the effect on the sensor response when acquiring data at the single center wavelength of 853 nm. FIG. 8 shows the optimal center imaging wavelength as a function of change in refractive index from a base refractive index of water. An imaging wavelength of 853 nm is only optimal for a change in refractive index of ~$3 \times 10^{-3}$. However, for changes in refractive index of $<3 \times 10^{-3}$ the response measured at a center wavelength of 853 nm is near that expected at the optimal center imaging wavelength. For larger changes in refractive index, the response measured at a center imaging wavelength of 853 nm is significantly less than that expected at the optimal center imaging wavelength, up to ~10% decrease for a change in sample refractive index of 0.01.

Figure 9:
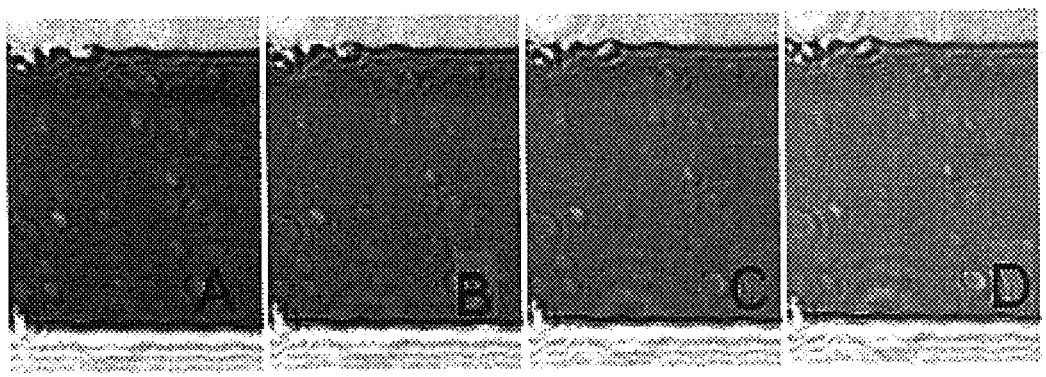
FIG. 9 shows a series of normalized images of sucrose solutions having a range of various refractive indexes measured by an exemplary sensor of the present invention.
Figure 10:
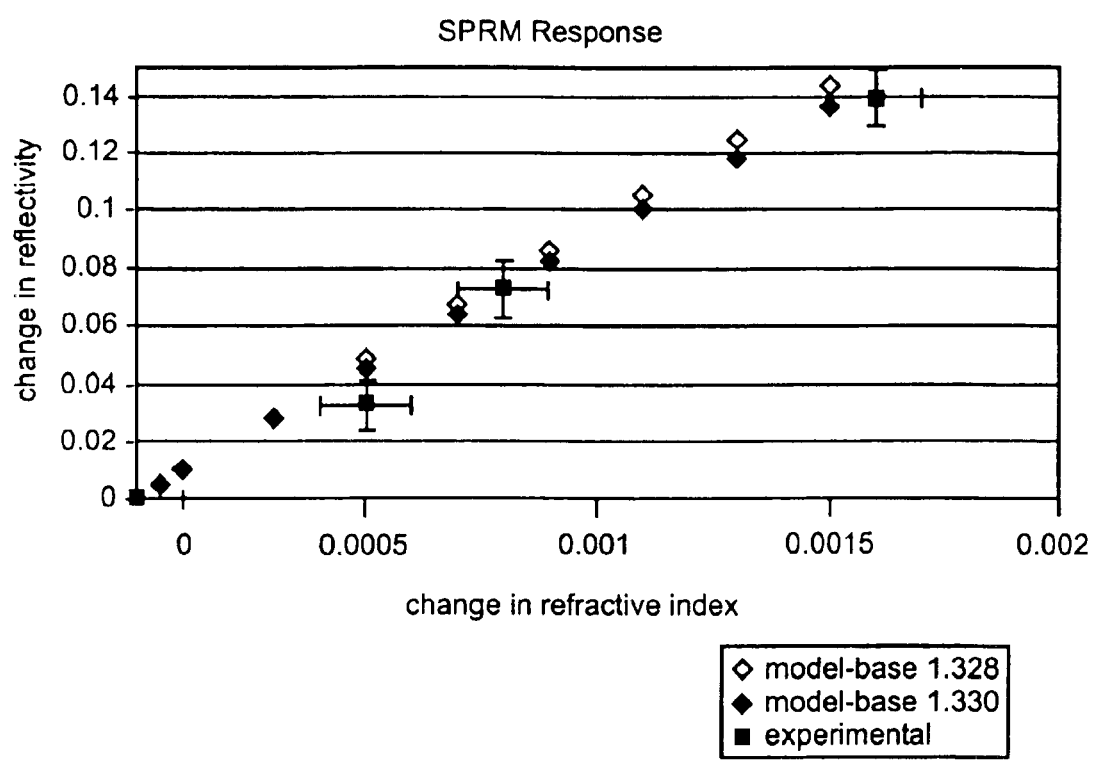
FIG. 10 shows a plot of the experimental response of an exemplary SPR sensor. As shown, the response of the system is linear for changes in refractive indices less than $3 \times 10^{-3}$.

The experimental response of the exemplary SPR sensor was investigated using a series of low concentration sucrose (Sigma-Aldrich Inc., St. Louis, Mo.) solutions. The refractive index of each sucrose solution was measured with a refractometer (Milton Roy Company, Ivyland, Pa.). The system uses standard size soda lime glass microscope slides (Fisher Scientific, Hampton, N.H.), cleaned in Nanostrip™ solution, and then deposited with 1 nm Cr and 450 nm Au. Before use on the imaging system, the Au coated slides were cleaned in a 1:1:5 solution of 30% hydrogen peroxide, ammonium hydroxide, and ddI water. The slides were then placed in a 0.2 mM ethyleneglycol-terminated thiol solution for 24–72 hours in a darkened, nitrogen atmosphere to allow for the formation of a non-fouling self-assembled monolayer. FIG. 9 shows a series of normalized images of solutions of various refractive indexes. All images were taken with a center imaging wavelength of ~850 nm. The images A through D show the same region of the flow reactor with solutions of refractive index 1.3338, 1.3343, 1.3346, and 1.3354, respectively. After the introduction of each sucrose solution, the reactor and system was flushed with ddI water. Analysis of the signal in the region after each ddI water rinse indicates little nonspecific adsorption, ≦7% variation in the signal. FIG. 10 shows a plot of the experimental response of an exemplary SPR sensor. As shown, the response of the system is linear for changes in refractive indexes $<3 \times 10^{-3}$.

The detection limit of the exemplary SPR sensor was investigated using a sample of ddI water. Images were taken at 2 sec intervals and an exposure time of 1.2 s over a time period of ~3 minutes. The p-polarized images were normalized with an s-polarized image to obtain percent reflectivity using an s-polarized image and data averaged from an area of 100 pixels. The water sample showed a 50% reflectivity with a standard deviation of 0.13%. Thus, the detection limit of the instrument is ~4 times this standard deviation, or 0.5%. This reflectivity corresponds to a lower limit in the detectable change in refractive index of ~$5 \times 10^{-5}$.

Figure 11:
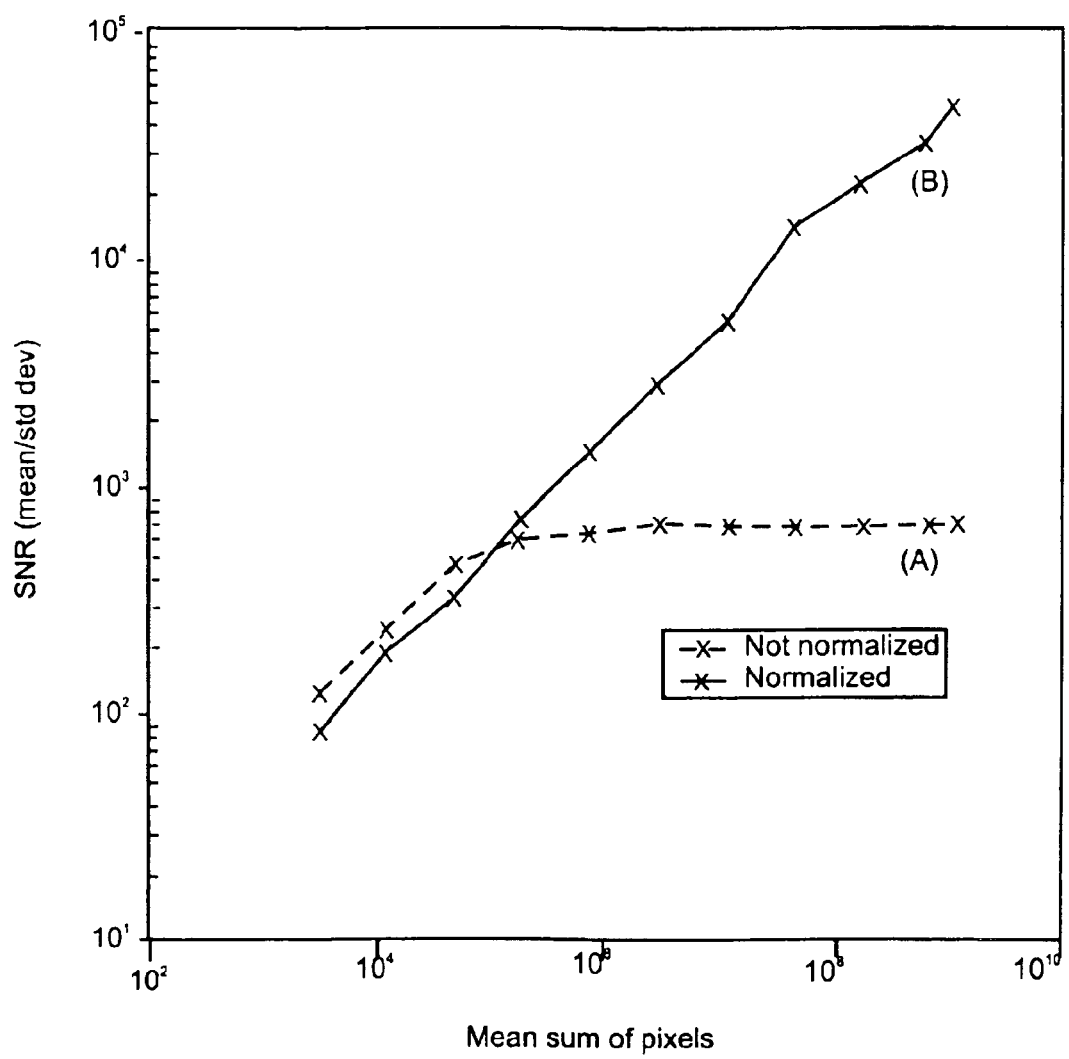
FIG. 11 shows the signal-to-noise ratio as a function of number of pixels averaged for both uncorrected (A, bottom plot) and corrected (B, top plot) SPR data.

No further increases in the signal to noise ratio (SNR) were obtained by averaging over >100 pixels unless the signal was also normalized for temporal changes in the SPR sensor. With the appropriate reference normalization, however, the SNR increases, as expected, with the square of the signal intensity. FIG. 11 shows the SNR ratio as a function of number of pixels averaged for both uncorrected (A, bottom plot) and corrected (B, top plot) data SPR data. The data consisted of a series of 100 images (800 ms exposure time) of the source beam taken at 2 s intervals. Specifically, a factor of $10^2$ increase in the intensity of our signal would yield a factor of 10 increase in the SNR or a detection limit of ~$5 \times 10^{-6}$. Additionally, the SNR was increased further by hardware modifications to the system that result in an increase in the source intensity.

EXAMPLE 2

SPR Images of Thiol Patterns and Protein Bovine Serum Albumin on Gold Surfaces

Figures 12A, 12B, 12C, 12D, 12E:
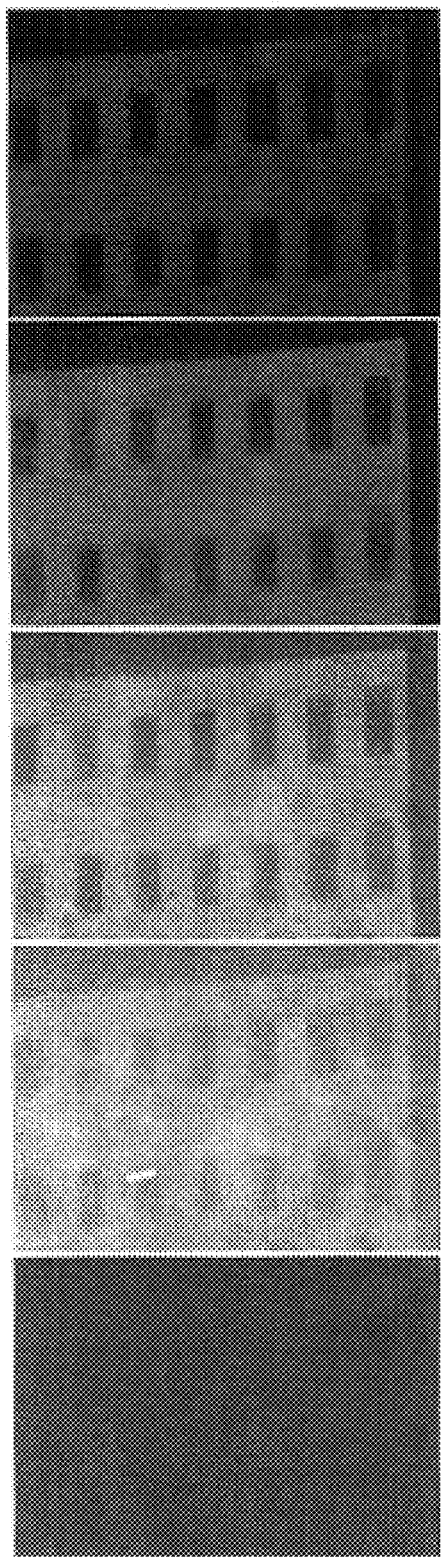
FIG. 12A corresponds to a center wavelength of 857 nm, FIG. 12B corresponds to a center wavelength of 852 nm, FIG. 12C corresponds to a center wavelength of 845 nm, FIG. 12D corresponds to a center wavelength of 830 nm and FIG. 12E corresponds to a center wavelength of 814 nm.

To assess the sensitivity and spatial resolution of SPR imaging devices of the present invention, SPR images of thiol patterns were generated by an exemplary SPR sensor. Thiol patterns on a gold surface (comprising approximately 1 nm Cr and approximately 45 nm Au electron beam deposited onto standard microscope slide from Fisher Scientific) was made using a polydimethylsiloxane (PDMS) stamping protocol. The protocol employed was optimized to minimize transfer of material from the PDMS stamp to the surface and to produce one monolayer of thiol on the surface. All images were taken with p-polarized light. FIG. 12 shows a series of images taken of a thiol and water pattern with an optical interference filter positioned a several different tilt angles. FIG. 12A corresponds to a center wavelength of 857 nm, FIG. 12B corresponds to a center wavelength of 852 nm, FIG. 12C corresponds to a center wavelength of 845 nm, FIG. 12D corresponds to a center wavelength of 830 nm and FIG. 12E corresponds to a center wavelength of 814 nm. The hexadecanethiol layers correspond to the light regions of the images and the water layers correspond to the dark regions. Square regions created by contact with the stamps, approximately 500 µm by 212 µm. As illustrated by FIG. 12A to 12E as the filter is tilted away from optimal position for this sample, the contrast between regions of different refractive indices decreases. As illustrated in FIG. 12A, SPR sensors of the present invention are capable generating high optical quality images of a probe region having refractive indices.

An upper limit to the lateral resolution of less than approximately 50 µm was experimentally determined for the exemplary SPR sensor. FIG. 13 shows images of thiol patterns with minimum feature sizes of approximately 100 µm (A, left side) and approximately 50 µm (B, right side). The image shows one dimension foreshortened by a factor of 0.43. In the direction of surface plasmon propagation, the lower limit to the lateral resolution was determined to be >50 µm. This is in agreement with the known surface plasmon propagation length on Au in the near infrared.

Figure 14A:
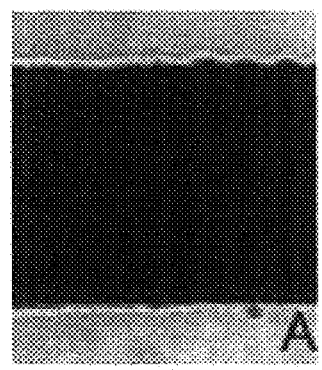
FIGS. 14A–D show images generated upon the adsorption of protein bovine serum albumin (BSA) onto a gold surface. The image in FIG. 14A shows a small region of the reactor with a background of water.
Figure 14B:
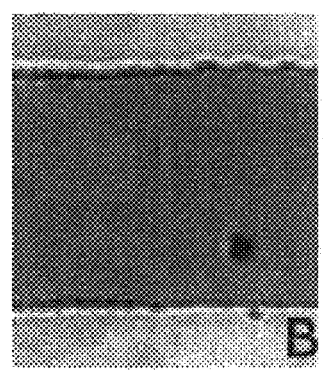
Figure 14C:
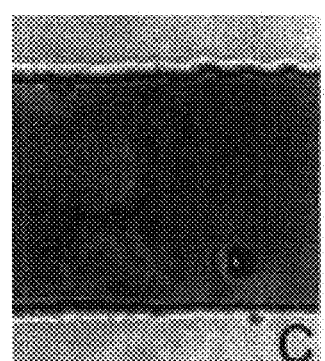
Figure 14D:
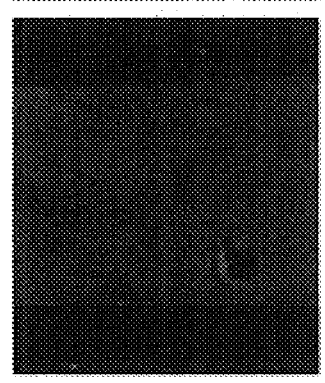

FIGS. 14A–D show images generated upon the adsorption of protein bovine serum albumin (BSA) onto a gold surface. All images were taken with p-polarized light and a center wavelength of about 853 nm. The image in FIG. 14A shows a small region of the reactor with a background of water ($RI_{water}$ is about 1.328 at about 850 nm). FIG. 14B shows an image of the same region of the reactor with a 2 mg ml$^{-1}$ solution of BSA in phosphate buffered saline (PBS). FIG. 14C shows an image of the same region with a background of water after pumping water through the reactor to remove all unbound protein. FIG. 14D shows a difference image resulting from subtraction of images in FIG. 14A and FIG. 14C. The refractive index change is due to the adsorption of protein onto the Au surface (for a monolayer of BSA in water, RI is about 1.331). This change in refractive index corresponds to a change in percent reflectivity of about 26%. These measurements show that SPR sensors of the present invention are capable of the sensitive detection of changes in refractive index due to adsorption of protein in the probe region.

We claim:

1. A surface plasmon resonance sensor for sensing the refractive index of a probe region comprising:
    a polychromatic light source for generating light propagating along an incident light propagation axis;
    a polarizer in optical communication with said polychromatic light source for selecting the polarization state of said light;
    an optical assembly in optical communication with said polychromatic light source, said optical assembly comprising a dielectric layer, a dielectric sample layer and a conducting layer positioned between said dielectric layer and said dielectric sample layer, wherein illumination of said optical assembly with said light generates light propagating along a reflected light propagation axis, wherein a portion of said dielectric sample layer adjacent to said conducting film comprises the probe region;
    a detector in optical communication with said optical assembly for detecting said light propagating along said reflected light axis, thereby sensing the refractive index of said probe region; and
    a selectably adjustable optical interference filter positioned in the optical path between said light source and said detector for transmitting light having a distribution of transmitted wavelengths selected to generate surface plasmons on a surface of said conducting layer in contact with said dielectric sample layer, wherein the distribution of transmitted wavelengths is continuously tunable by adjustment of the optical interference filter,
    wherein said optical interference filter is rotationally adjustable about an axis which is orthogonal to said incident light propagation axis, wherein rotation of said optical interference filter selectably adjusts the tilt angle and distribution of transmitted wavelengths of said optical interference filter.

2. The surface plasmon resonance sensor of claim 1 further comprising a light collection and focusing element positioned between said optical assembly and said detector, said light collection and focusing element for collecting said light propagating along the reflected light propagation axis and focusing light propagating along the reflected light propagation axis onto said detector.

3. The surface plasmon resonance sensor of claim 1 further comprising a collimating optical element for collimating light from said polychromatic light source, wherein said collimating optical element is positioned between said polychromatic light element and said optical assembly.

4. The surface plasmon resonance sensor of claim 3 where said collimating optical element comprises a first lens, a pinhole, and a second lens each positioned between said polychromatic light source and said optical assembly.

5. The surface plasmon resonance sensor of claim 1 wherein said optical interference filter is positioned between said polychromatic light source and said optical assembly.

6. The surface plasmon resonance sensor of claim 1 wherein said optical interference filter is a Fabry-Perot etalon.

7. The surface plasmon resonance sensor of claim 1 wherein said optical interference filter is a linearly variable interference filter.

8. The surface plasmon resonance sensor of claim 1 wherein rotation of said optical interference filter selectably adjusts the center wavelength of the distribution of transmitted wavelengths.

9. The surface plasmon resonance sensor of claim 8 wherein said center wavelength of the distribution of transmitted wavelengths is provided by the equation:

$$\lambda_{center}(\theta_{tilt}) = (\lambda_{center}(0))\left(1 - \left(\frac{\sin^2\theta_{tilt}}{n^2}\right)\right)^{0.5}$$

wherein $\lambda_{center}$ is said center wavelength of the distribution of transmitted wavelengths, $\theta_{tilt}$ is a tilt angle, $\lambda_{center}(0)$ is a center wavelength at normal incidence with respect to the reflected or incident light propagation axes and n is the refractive index of the optical interference filter.

10. The surface plasmon resonance sensor of claim 1 wherein said distribution of transmitted wavelengths is characterized by a center wavelength and said center wavelength is tunable over a range of about 65 nm.

11. The surface plasmon resonance sensor of claim 1 wherein said distribution of transmitted wavelengths is characterized by a bandwidth and said bandwidth has a value selected from a range of about 1 nm to about 100 nm.

12. The surface plasmon resonance sensor of claim 1 wherein said detector is a charge coupled device.

13. The surface plasmon resonance sensor of claim 1 wherein said dielectric layer has a first refractive index, wherein said dielectric sample layer has a second refractive index which is less than said first refractive index and wherein said light propagating along said incident light propagation axis undergoes total internal reflection upon interaction with said optical assembly.

14. The surface plasmon resonance sensor of claim 1 wherein said dielectric layer is a prism.

15. The surface plasmon resonance sensor of claim 1 further comprising a flow cell operationally connected to said optical assembly for introducing a sample into said probe region.

16. The surface plasmon resonance sensor of claim 15 wherein said dielectric sample layer is a sample provided by said flow cell.

17. The surface plasmon resonance sensor of claim 1 wherein said conducting layer comprises a gold film.

18. The surface plasmon resonance sensor of claim 1 wherein said dielectric layer and said conducting layer comprise of a waveguide.

19. The surface plasmon resonance sensor of claim 1 wherein said dielectric layer and said conducting layer comprise of an optical fiber.

20. The surface plasmon resonance sensor of claim 1 comprising a surface plasmon imaging device.

21. The surface plasmon resonance sensor of claim 1 wherein said light source is an incoherent light source.

22. The surface plasmon resonance sensor of claim 1 further comprising a microfluidic flow cell operationally connected to said optical assembly for introducing a sample into said probe region.

23. The surface plasmon resonance sensor of claim 22 wherein said surface of said conducting layer in contact with said dielectric sample layer comprises a side of said microfluidic flow cell.

24. The surface plasmon resonance sensor of claim 1 wherein said surface of said conducting layer is modified to provide for selective binding affinity.

25. The surface plasmon resonance sensor of claim 1 wherein said surface of said conducting layer in contact with said dielectric sample layer is modified to provide for selective adsorption characteristics.

26. A method of sensing the refractive index of a probe region comprising the steps of:
passing light from a polychromatic light source through a polarizer, thereby generating light propagating along an incident light propagation axis;
directing said light onto an optical assembly, said optical assembly comprising a dielectric layer, a dielectric sample layer and a conducting layer positioned between said dielectric layer and said dielectric sample layer, thereby generating light propagating along a reflected light propagation axis, wherein a portion of said dielectric sample layer adjacent to said conducting layer comprises said probe region;
passing said light through a selectably adjustable optical interference filter positioned in the optical path between said light source and a detector, wherein light having a distribution of transmitted wavelengths is transmitted through said optical interference filter;
detecting said light having said distribution of transmitted wavelengths with said detector, and
tuning the center wavelength of said distribution of transmitted wavelengths by adjusting said optical interference filter to transmit light having a continuously tunable distribution of wavelengths that generates surface plasmons on a surface of said conducting layer in contact with said dielectric sample layer, thereby sensing said refractive index of said probe region,
wherein said adjusting step comprises the step of rotating said optical interference filter about an axis which is orthogonal to said incident light propagation axis, wherein rotation of said optical interference filter selectably adjusts the tilt angle of said interference filter and the distribution of wavelengths of light which are transmitted by said interference filter.

27. The method of claim 26 wherein said adjusting step comprises the step of systematically varying said distribution of wavelengths transmitted by said optical interference filter.

28. The method of claim 26 wherein said adjusting step comprises the steps of:
transmitting light through said optical interference filter having a first distribution of wavelengths, thereby generating a first image of said probe region;
transmitting light through said optical interference filter having a second distribution of wavelengths, thereby generating a second image of said probe region;
comparing the spectral quality of said first and second images; and
selecting a distribution of wavelengths of said incident light which are transmitted by said optical interference filter to enhance the spectral quality of said image.

29. The method of claim 26 wherein said optical interference filter is positioned between said light source and said optical assembly.

30. The method of claim 26 wherein said optical interference filter is a Fabry-Perot etalon.

31. The method of claim 26 wherein said step of passing light through a polarizer generates light having a p-polarization state propagating along said incident light propagation axis.

32. The method of claim 26 where said light propagating along said incident light propagation axis undergoes total internal reflection upon interaction with said optical assembly.

33. The method of claim 26 further comprising the step of collimating light from said polychromatic optical source.

34. The method claim 26 further comprising the step of focusing said light propagating along said reflected light propagation axis onto said detector.

35. The method of claim 26 wherein said light has wavelengths in the near infrared region of the electromagnetic spectrum.

36. The method of claim 26 wherein said optical assembly further comprises a flow cell operationally connected to said probe region for delivering chemical species into said probe region.

37. The method of claim 36 further comprising the step of flowing chemical species through said flow cell, thereby changing the composition of said probe region.

38. The method of claim 36 further comprising the step of flowing chemical species through said flow cell, thereby changing the refractive index of said probe region.

39. The method of claim 36 further comprising the step of flowing chemical species through said flow cell, thereby changing the thickness of said probe region.

40. The method of claim 36 wherein said flow cell is a microfluidic flow cell.

41. A method of sensing the refractive index of a probe region comprising the steps of:

passing light from a polychromatic light source through a polarizer, thereby generating p-polarized light or s-polarized light propagating along an incident light propagation axis;

directing said light onto an optical assembly, said optical assembly comprising a dielectric layer, a dielectric sample layer and a conducting layer positioned between said dielectric layer and said dielectric sample layer, wherein light is reflected by said optical assembly thereby generating reflected light propagating along a reflected light propagation axis, wherein a portion of said dielectric sample layer adjacent to said conducting layer comprises said probe region;

passing said light through an optical interference filter positioned in the optical path between said light source and a detector, wherein said optical interference filter has a tilt angle with respect to said incident light propagation axis or said reflected light propagation axis selected so that said optical interference filter transmits incident light having a distribution of wavelengths that generates surface plasmons on a surface of said conducting layer in contact with said dielectric sample layer;

detecting said reflected light using said detector, thereby measuring a first intensity of reflected light corresponding to p-polarized light and measuring a second intensity of reflected light corresponding reflected s-polarized light;

calculating an observed percent reflectivity by determining the ratio of said first intensity of reflected light to said second intensity of reflected light;

determining a correction factor by measuring the ratio of the intensity of p-polarized light transmitted by said optical interference filter to s-polarized light transmitted by said optical interference filter having said tilt angle; and calculating a percent reflectivity corrected for polarization dependent transmission of light transmitted by said optical interference filter by dividing said observed percent reflectivity by said correction factor, thereby sensing the refractive index of said probe region.

42. The method of claim 41 further comprising the steps of:

determining a plurality of correction factors corresponding to different tilt angles by measuring the ratios of the intensity of p-polarized light transmitted by said optical interference filter to s-polarized light transmitted by said optical interference filter having a plurality of tilt angles;

plotting said correction factors as a function of tilt angle, thereby generating a calibration plot;

fitting a curve to said calibration plot, thereby generating a calibration curve; and determining said correction factor using said calibration curve.

43. The method of claim 41 where said step of determining said correction factor by measuring the ratio of the intensity of p-polarized light transmitted by said optical interference filter to s-polarized light transmitted by said optical interference filter having said tilt angle is carried out by separately measuring the intensities of p-polarized light and s-polarized light passed by said interference filter in the absence of surface plasmon formation.

44. A method of generating an image of a probe region comprising the steps of:

passing light from a polychromatic light source through a polarizer, thereby generating p-polarized light or s-polarized light propagating along an incident light propagation axis;

directing said light onto an optical assembly, said optical assembly comprising a dielectric layer, a dielectric sample layer and a conducting layer positioned between said dielectric layer and said dielectric sample layer, wherein light is reflected by said optical assembly thereby generating reflected light propagating along a reflected light propagation axis, wherein a portion of said dielectric sample layer adjacent to said conducting layer comprises said probe region;

passing said light through an optical interference filter positioned in the optical path between said light source and a detector, wherein said optical interference filter has a tilt angle with respect to said incident light propagation axis or said reflected light propagation axis selected so that said optical interference filter transmits incident light having a distribution of wavelengths that generates surface plasmons on a surface of said conducting layer in contact with said dielectric sample layer;

detecting said reflected light using said detector, thereby measuring a first two-dimensional distribution of reflected light intensities corresponding to p-polarized light and measuring second two-dimensional distribution of reflected light intensities corresponding to s-polarized light;

calculating a two dimensional distribution of observed percent reflectivities by determining the ratios of p-polarized reflected light intensities in said first two-dimensional distribution to s-polarized light intensities in said second two-dimensional distributions of reflected light intensities;

determining a two-dimensional array of correction factors corresponding to said tilt angle by measuring the ratios of the intensity of p-polarized light transmitted by said optical interference filter to s-polarized light transmitted by said optical interference filter having said tilt angle for each element in said two dimensional distribution of reflected light intensities ; and calculating a two dimensional distribution of percent reflectivities corrected for polarization dependent transmission of light transmitted by said optical interference filter by dividing said observed percent reflectivities by said correction factors in said two dimensional array, thereby generating an image of said probe region.

45. The method of claim 44 further comprising the steps of:

determining a plurality of two dimensional arrays of correction factors corresponding to different tilt angles by measuring the ratios of the intensity of p-polarized light transmitted by said optical interference filter to s-polarized light transmitted by said optical interference filter at a plurality of tilt angles;

plotting said correction factors as a function of tilt angle, thereby generating a plurality of calibration plots;

fitting curves to said calibration plots, thereby generating a plurality of calibration curves; and determining said correction factors using said plurality of said calibration curves.

46. The method of claim 44 further comprising the step of optimizing the contrast of said image of said probe region by varying the center wavelength of said distribution of transmitted wavelength by rotating said optical interference filter about an axis which is orthogonal to said incident light propagation axis or said reflected light propagation axis.

47. The method of claim 44 where said step of determining a two-dimensional array of correction factors corresponding to said tilt angle by measuring the ratios of the intensity of p-polarized light transmitted by said optical interference filter to s-polarized light transmitted by said optical interference filter having said tilt angle for each element in said two dimensional distribution of reflected light intensities is carried out by separately measuring the intensities of p-polarized light and s-polarized light passed by said interference filter in the absence of surface plasmon formation.

48. A surface plasmon resonance sensor for sensing the refractive index of a probe region comprising:
a polychromatic light source for generating light propagating along an incident light propagation axis;
a polarizer in optical communication with said polychromatic light source for selecting the polarization state of said light;
an optical assembly in optical communication with said polychromatic light source, said optical assembly comprising a dielectric layer, a dielectric sample layer and a conducting layer positioned between said dielectric layer and said dielectric sample layer, wherein illumination of said optical assembly with said light generates light propagating along a reflected light propagation axis, wherein a portion of said dielectric sample layer adjacent to said conducting film comprises the probe region;
a detector in optical communication with said optical assembly for detecting said light propagating along said reflected light axis, thereby sensing the refractive index of said probe region; and
an optical interference filter positioned in the optical path between said light source and said detector for transmitting light having a distribution of transmitted wavelengths selected to generate surface plasmons on a surface of said conducting layer in contact with said dielectric sample layer, wherein the distribution of transmitted wavelengths is continuously tunable by adjustment of the optical interference filter,
wherein said optical interference filter is rotationally adjustable about an axis which is orthogonal to said reflected light propagation axis, wherein rotation of said optical interference filter selectably adjusts the tilt angle and distribution of transmitted wavelengths of said optical interference filter.

49. The surface plasmon resonance sensor of claim 48 wherein said optical interference filter has first and second substantially parallel ends and said first end has a tilt angle selected over a range of 0° to about 35°.

50. The surface plasmon resonance sensor of claim 48 wherein said distribution of transmitted wavelengths is characterized by a center wavelength and said center wavelength is tunable over a range of about 65 nm.

51. The surface plasmon resonance sensor of claim 48 wherein said distribution of transmitted wavelengths is characterized by a bandwidth and said bandwidth has a value selected from a range of about 1 nm to about 100 nm.

52. A surface plasmon resonance sensor for sensing the refractive index of a probe region comprising:
a polychromatic light source for generating light propagating along an incident light propagation axis;
a polarizer in optical communication with said polychromatic light source for selecting the polarization state of said light;
an optical assembly in optical communication with said polychromatic light source, said optical assembly comprising a dielectric layer, a dielectric sample layer and a conducting layer positioned between said dielectric layer and said dielectric sample layer, wherein illumination of said optical assembly with said light generates light propagating along a reflected light propagation axis, wherein a portion of said dielectric sample layer adjacent to said conducting film comprises the probe region;
a detector in optical communication with said optical assembly for detecting said light propagating along said reflected light axis, thereby sensing the refractive index of said probe region; and
an optical interference filter positioned in the optical path between said light source and said detector for transmitting light having a distribution of transmitted wavelengths selected to generate surface plasmons on a surface of said conducting layer in contact with said dielectric sample layer, wherein the distribution of transmitted wavelengths is continuously tunable by adjustment of the optical interference filter,
wherein said optical interference filter is rotationally adjustable about an axis which is orthogonal to said incident light propagation axis, wherein rotation of said optical interference filter selectably adjusts the distribution of wavelengths that are substantially prevented from transmitting through said optical interference filter.

53. The surface plasmon resonance sensor of claim 52 wherein said optical interference filter has first and second substantially parallel ends and said first end has a tilt angle selected over a range of 0° to about 35°.

54. The surface plasmon resonance sensor of claim 52 wherein said distribution of transmitted wavelengths is characterized by a center wavelength and said center wavelength is tunable over a range of about 65 nm.

55. The surface plasmon resonance sensor of claim 52 wherein said distribution of transmitted wavelengths is characterized by a bandwidth and said bandwidth has a value selected from a range of about 1 nm to about 100 nm.

56. A surface plasmon resonance sensor for sensing the refractive index of a probe region comprising:
a polychromatic light source for generating light propagating along an incident light propagation axis;
a polarizer in optical communication with said polychromatic light source for selecting the polarization state of said light;
an optical assembly in optical communication with said polychromatic light source, said optical assembly comprising a dielectric layer, a dielectric sample layer and a conducting layer positioned between said dielectric layer and said dielectric sample layer, wherein illumination of said optical assembly with said light generates light propagating along a reflected light propagation axis, wherein a portion of said dielectric sample layer adjacent to said conducting film comprises the probe region;
a detector in optical communication with said optical assembly for detecting said light propagating along said reflected light axis, thereby sensing the refractive index of said probe region; and an optical interference filter positioned in the optical path between said light source and said detector for transmitting light having a distribution of transmitted wavelengths selected to generate surface plasmons on a surface of said conducting layer in contact with said dielectric sample layer, wherein the distribution of transmitted wavelengths is continuously tunable by adjustment of the optical interference filter, wherein said optical interference filter is rotationally adjustable about an axis which is orthogonal to said reflected light propagation axis, wherein rotation of said optical interference filter selectably adjusts the distribution of wavelengths that are substantially prevented from transmitting through said optical interference filter.

57. The surface plasmon resonance sensor of claim 56 wherein said optical interference filter has first and second substantially parallel ends and said first end has a tilt angle selected over a range of 0° to about 35°.

58. The surface plasmon resonance sensor of claim 56 wherein said distribution of transmitted wavelengths is characterized by a center wavelength and said center wavelength is tunable over a range of about 65 nm.

59. The surface plasmon resonance sensor of claim 56 wherein said distribution of transmitted wavelengths is characterized by a bandwidth and said bandwidth has a value selected from a range of about 1 nm to about 100 nm.

60. A surface plasmon resonance sensor for sensing the refractive index of a probe region comprising:

a polychromatic light source for generating light propagating along an incident light propagation axis;

a polarizer in optical communication with said polychromatic light source for selecting the polarization state of said light;

an optical assembly in optical communication with said polychromatic light source, said optical assembly comprising a dielectric layer, a dielectric sample layer and a conducting layer positioned between said dielectric layer and said dielectric sample layer, wherein illumination of said optical assembly with said light generates light propagating along a reflected light propagation axis, wherein a portion of said dielectric sample layer adjacent to said conducting film comprises the probe region;

a detector in optical communication with said optical assembly for detecting said light propagating along said reflected light axis, thereby sensing the refractive index of said probe region; and an optical interference filter positioned in the optical path between said light source and said detector for transmitting light having a distribution of transmitted wavelengths selected to generate surface plasmons on a surface of said conducting layer in contact with said dielectric sample layer, wherein the distribution of transmitted wavelengths is continuously tunable by adjustment of the optical interference filter, wherein said optical interference filter has first and second substantially parallel ends and said first end has a tilt angle selected over the range of 0° to about 35°.

61. The surface plasmon resonance sensor of claim 60 wherein said optical interference filter has first and second substantially parallel ends and said first end has a tilt angle selected over a range of 0° to about 35°.

62. The surface plasmon resonance sensor of claim 60 wherein said distribution of transmitted wavelengths is characterized by a center wavelength and said center wavelength is tunable over a range of about 65 nm.

63. The surface plasmon resonance sensor of claim 60 wherein said distribution of transmitted wavelengths is characterized by a bandwidth and said bandwidth has a value selected from a range of about 1 nm to about 100 nm.

64. A method of sensing the refractive index of a probe region comprising the steps of:

passing light from a polychromatic light source through a polarizer, thereby generating light propagating along an incident light propagation axis;

directing said light onto an optical assembly, said optical assembly comprising a dielectric layer, a dielectric sample layer and a conducting layer positioned between said dielectric layer and said dielectric sample layer, thereby generating light propagating along a reflected light propagation axis, wherein a portion of said dielectric sample layer adjacent to said conducting layer comprises said probe region;

passing said light through an optical interference filter positioned in the optical path between said light source and a detector, wherein light having a distribution of transmitted wavelengths is transmitted through said optical interference filter;

detecting said light having said distribution of transmitted wavelengths with said detector, and tuning the center wavelength of said distribution of transmitted wavelengths by adjusting said optical interference filter to transmit light having a continuously tunable distribution of wavelengths that generates surface plasmons on a surface of said conducting layer in contact with said dielectric sample layer, thereby sensing said refractive index of said probe regions, wherein said adjusting step comprises the step of rotating said optical interference filter about an axis which is orthogonal to said reflected light propagation axis, wherein rotation of said optical interference filter selectably adjusts the tilt angle of said interference filter and the distribution of wavelengths of light which are transmitted by said interference filter.

65. The method of claim 64 wherein said adjusting step comprises the steps of:

transmitting light through said optical interference filter having a first distribution of wavelengths, thereby generating a first image of said probe region;

transmitting light through said optical interference filter having a second distribution of wavelengths, thereby generating a second image of said probe region;

comparing the spectral quality of said first and second images; and selecting a distribution of wavelengths of said incident light which are transmitted by said optical interference filter to enhance the spectral quality of said image.

66. The method of claim 64 wherein said adjusting step comprises the step of systematically varying said distribution of wavelengths transmitted by said optical interference filter.

67. A method of sensing the refractive index of a probe region comprising the steps of:

passing light from a polychromatic light source through a polarizer, thereby generating light propagating along an incident light propagation axis;

directing said light onto an optical assembly, said optical assembly comprising a dielectric layer, a dielectric sample layer and a conducting layer positioned between said dielectric layer and said dielectric sample layer, thereby generating light propagating along a reflected light propagation axis, wherein a portion of said dielectric sample layer adjacent to said conducting layer comprises said probe region;

passing said light through an optical interference filter positioned in the optical path between said light source and a detector, wherein light having a distribution of transmitted wavelengths is transmitted through said optical interference filter;

detecting said light having said distribution of transmitted wavelengths with said detector, and tuning the center wavelength of said distribution of transmitted wavelengths by adjusting said optical interference filter to transmit light having a continuously tunable distribution of wavelengths that generates surface plasmons on a surface of said conducting layer in contact with said dielectric sample layer, thereby sensing said refractive index of said probe region, wherein said adjusting step comprises the step of rotating said optical interference filter about an axis which is orthogonal to said incident light propagation axis, wherein rotation of said optical interference filter selectably adjusts the tilt angle of said interference filter and the distribution of wavelengths that are substantially prevented from transmitting through said optical interference filter.

68. The method of claim 67 wherein said adjusting step comprises the steps of:

transmitting light through said optical interference filter having a first distribution of wavelengths, thereby generating a first image of said probe region;

transmitting light through said optical interference filter having a second distribution of wavelengths, thereby generating a second image of said probe region;

comparing the spectral quality of said first and second images; and selecting a distribution of wavelengths of said incident light which are transmitted by said optical interference filter to enhance the spectral quality of said image.

69. The method of claim 67 wherein said adjusting step comprises the step of systematically varying said distribution of wavelengths transmitted by said optical interference filter.

70. A method of sensing the refractive index of a probe region comprising the steps of:

passing light from a polychromatic light source through a polarizer, thereby generating light propagating along an incident light propagation axis;

directing said light onto an optical assembly, said optical assembly comprising a dielectric layer, a dielectric sample layer and a conducting layer positioned between said dielectric layer and said dielectric sample layer, thereby generating light propagating along a reflected light propagation axis, wherein a portion of said dielectric sample layer adjacent to said conducting layer comprises said probe region;

passing said light through an optical interference filter positioned in the optical path between said light source and a detector, wherein light having a distribution of transmitted wavelengths is transmitted through said optical interference filter;

detecting said light having said distribution of transmitted wavelengths with said detector, and tuning the center wavelength of said distribution of transmitted wavelengths by adjusting said optical interference filter to transmit light having a continuously tunable distribution of wavelengths that generates surface plasmons on a surface of said conducting layer in contact with said dielectric sample layer, thereby sensing said refractive index of said probe region, wherein said adjusting step comprises the step of rotating said optical interference filter about an axis which is orthogonal to said reflected light propagation axis, wherein rotation of said optical interference filter selectably adjusts the tilt angle of said interference filter and the distribution of wavelengths that are substantially prevented from transmitting through said optical interference filter.

71. The method of claim 70 wherein said adjusting step comprises the steps of:

transmitting light through said optical interference filter having a first distribution of wavelengths, thereby generating a first image of said probe region;

transmitting light through said optical interference filter having a second distribution of wavelengths, thereby generating a second image of said probe region;

comparing the spectral quality of said first and second images; and selecting a distribution of wavelengths of said incident light which are transmitted by said optical interference filter to enhance the spectral quality of said image.

* * * * *

UNITED STATES PATENT AND TRADEMARK OFFICE
CERTIFICATE OF CORRECTION

| | | |
|---|---|---|
| PATENT NO. | : 7,030,989 B2 | Page 1 of 1 |
| APPLICATION NO. | : 10/696738 | |
| DATED | : April 18, 2006 | |
| INVENTOR(S) | : Paul Yager and Elain S. Fu | |

It is certified that error appears in the above-identified patent and that said Letters Patent is hereby corrected as shown below:

Column 1, line 16, pleae delete "1UO1 DE14971-01" and insert --U01 DE014971--.

Signed and Sealed this

Fifth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,030,989 B2  Page 1 of 1
APPLICATION NO. : 10/696738
DATED : April 18, 2006
INVENTOR(S) : Paul Yager and Elain S. Fu It is certified that error appears in the above-identified patent and that said Letters Patent is hereby corrected as shown below:

Column 1, line 15, please delete, "The work was funded through a grant by the United States government under NIDCR grant 1UO1 DE14971-01"

and insert

-- This invention was made with government support under grant number U01 DE014971 awarded by National Institutes of Health. The government has certain rights in the invention. --

Signed and Sealed this

Twenty-sixth Day of August, 2008

JON W. DUDAS
*Director of the United States Patent and Trademark Office*